(12) United States Patent
Tirtowidjojo et al.

(10) Patent No.: US 8,129,436 B2
(45) Date of Patent: Mar. 6, 2012

(54) MIXED ALCOHOL SYNTHESIS WITH ENHANCED CARBON VALUE USE

(75) Inventors: Max M. Tirtowidjojo, Lake Jackson, TX (US); Barry B. Fish, Lake Jackson, TX (US); Hendrik L. Pelt, Terneuzen (NL); Dennis W. Jewell, Angleton, TX (US); Mark D. Bearden, Richland, WA (US); John G. Pendergast, Jr., Lake Jackson, TX (US); Jon H. Siddall, Midland, MI (US); Brien A. Stears, League City, TX (US); Haivan D. Tran, Pearland, TX (US); Jan W. Verwijs, Hoek (NL); Aaltje Verwijs-van den Brink, legal representative, Hoek (NL); Lena Verwijs, legal representative, Hoevelaken (NL); Hendrika Gerrita Verwijs, legal representative, Dordrecht (NL); Richard M. Wehmeyer, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 650 days.

(21) Appl. No.: 12/296,961

(22) PCT Filed: Mar. 21, 2007

(86) PCT No.: PCT/US2007/006967
§ 371 (c)(1),
(2), (4) Date: Oct. 13, 2008

(87) PCT Pub. No.: WO2008/048364
PCT Pub. Date: Apr. 24, 2008

(65) Prior Publication Data
US 2010/0069515 A1 Mar. 18, 2010

Related U.S. Application Data

(60) Provisional application No. 60/791,763, filed on Apr. 13, 2006.

(51) Int. Cl.
*C07C 27/00* (2006.01)
(52) U.S. Cl. ........ 518/700; 518/702; 518/705; 518/714; 518/715
(58) Field of Classification Search .................. 518/700, 518/702, 705, 714, 715
See application file for complete search history.

(56) References Cited

U.S. PATENT DOCUMENTS 631,622 A  8/1899  Dickerson
(Continued)

FOREIGN PATENT DOCUMENTS

EP  0172431  2/1986
(Continued)

OTHER PUBLICATIONS

Senol et al., Catalysis Today 100 (2005) 331-335.
(Continued)

*Primary Examiner* — Jafar Parsa (57) ABSTRACT

The present invention provides a method for simplifying manufacture of a mixed alcohol or mixed oxygenate product from synthesis gas. The mixed alcohol or mixed oxygenate product contains ethanol and other oxygenates with two or more carbon atoms per molecule. The method includes stripping a portion of carbon dioxide and inert gases contained in a mixed alcohol synthesis reaction product using a methanol-containing stream, such as one produced as part of the method, as a medium to absorb said carbon dioxide and inert gases and recycling light products and heavy products to one or more of synthesis gas generation, mixed alcohol synthesis and separation of desired mixed alcohol or mixed oxygenate products from other components of a mixed alcohol synthesis stream. The present invention also provides downstream processing of the mixed alcohol or mixed oxygenate product by subjecting the product to a dehydration step in order to convert at least ethanol, preferably at least ethanol and propanol, to their corresponding olefins (e.g. ethylene and propylene).

21 Claims, 1 Drawing Sheet

U.S. PATENT DOCUMENTS

| | | | |
|---|---|---|---|
| 1,859,244 A | 5/1932 | Patart | |
| 3,972,952 A | 8/1976 | Clark | |
| 4,607,055 A | 8/1986 | Grazioso et al. | |
| 4,607,056 A | 8/1986 | Grazioso et al. | |
| 4,616,040 A | 10/1986 | Grazioso et al. | |
| 4,625,049 A | 11/1986 | Current | |
| 4,661,525 A | 4/1987 | Grazioso et al. | |
| 4,675,344 A | 6/1987 | Conway et al. | |
| 4,749,724 A | 6/1988 | Quarderer et al. | |
| 4,752,622 A | 6/1988 | Stevens | |
| 4,752,623 A | 6/1988 | Stevens et al. | |
| 4,762,858 A | 8/1988 | Hucul et al. | |
| 4,775,696 A | 10/1988 | Prada-Silva et al. | |
| 4,825,013 A | 4/1989 | Quarderer et al. | |
| 4,831,060 A | 5/1989 | Stevens et al. | |
| 4,882,360 A | 11/1989 | Stevens | |
| 5,714,662 A | 2/1998 | Vora et al. | |
| 5,866,751 A | 2/1999 | Womack, Jr. et al. | |
| 6,130,260 A | 10/2000 | Hall et al. | |
| 6,248,796 B1 | 6/2001 | Jackson et al. | |
| 6,323,247 B1 | 11/2001 | Hall et al. | |
| 6,602,920 B2 | 8/2003 | Hall et al. | |
| 6,872,753 B2 | 3/2005 | Landis et al. | |
| 2003/0225169 A1 | 12/2003 | Yetman | |
| 2004/0122267 A1 | 6/2004 | Sher et al. | |
| 2005/0107481 A1 | 5/2005 | Janssen et al. | |
| 2005/0107482 A1 | 5/2005 | Van Egmond et al. | |
| 2005/0107651 A1 | 5/2005 | Sher et al. | |
| 2005/0113623 A1 | 5/2005 | Kuechler et al. | |
| 2005/0189212 A1 | 9/2005 | Morton | |

FOREIGN PATENT DOCUMENTS

| | | |
|---|---|---|
| EP | 0180719 | 5/1986 |
| EP | 0216472 | 4/1987 |
| EP | 0253540 | 1/1988 |
| EP | 0311297 | 4/1989 |
| EP | 0498573 | 8/1992 |
| GB | 2139224 | 11/1984 |
| GB | 2185907 | 8/1987 |
| WO | WO-99/15483 | 4/1999 |
| WO | WO-00/31004 | 6/2000 |
| WO | WO-01/44145 | 6/2001 |
| WO | WO-02/072741 | 9/2002 |
| WO | WO-03/084905 | 10/2003 |
| WO | WO-03/099961 | 12/2003 |
| WO | WO-2005/051872 | 6/2005 |
| WO | WO-2006/123158 | 11/2006 |
| WO | WO-2008/048364 | 4/2008 |

OTHER PUBLICATIONS

TSS Consultant in "Gridley Ethanol Demonstration Project Utilizing Biomass Gasification Technology: Pilot Plant Gasifier and Syngas Conversion Testing," Aug. 2002-Jun. 2004; National Renewable Energy Laboratory Report NREL/SR-510-37581. (Feb. 2005).

Spath et al. in "Preliminary Screening—Technical and Economic Assessment of Synthesis Gas to Fuels and Chemicals with Emphasis on the Potential for Biomass-Derived Syngas"; National Renewable Energy Laboratory Report NREL/TP-510-34929. (Dec. 2003); pp. 70-89.

Claus et al., Applied Catalysis A: General, 79 (1991) 1-18.

Cullinane et al., Chemical Engineering Science 59 (2004) 3619-3630.

Weiss, Gas Separation & Purification (1988) vol. 2, December, pp. 171-176.

Wender, Fuel Processing Technology, 48 (1996) 189-297.

Silvy et al., Applied Catalysis, 46 (1989), pp. 113-129.

Texier et al., Journal of Catalysis 223 (2004) pp. 404-418.

Laurent, et al., Applied Catalysis A: General 109 (1994) pp. 97-115.

Alberton et al., Catalysis Today 123 (2007) 257-264.

Kohl, et al., *Gas Purification*, 4$^{th}$ Ed. Gulf Publishing Co., 1985, pp. 148-149; 247-251; 265-267; 844-845; and 848-856.

MIXED ALCOHOL SYNTHESIS WITH ENHANCED CARBON VALUE USE

This application claims benefit of U.S. Provisional No. 60/791,763 filed Apr. 13, 2006.

The present invention relates generally to a process for converting synthesis gas (nominally a mixture of carbon monoxide (CO) and hydrogen ($H_2$)) into a mixture of alcohols, preferably using a sulfided cobalt/molybdenum (Co/Mo) catalyst such as cobalt/molybdenum disulfide (Co/$MoS_2$) or $CoMo_2S_x$, where x ranges from 4 to 6, with an average value of 5. The present invention relates particularly to such a process wherein natural gas is a preferred raw material for generation of synthesis gas. The present invention relates more particularly to such a process wherein methanol (MeOH) is recycled, preferably homologized to higher alcohols, rather than separated as a single product stream. The present invention also relates to such a process wherein a primary product is a mixture of ethanol (EtOH) and 1-propanol (PrOH), optionally in conjunction with a higher alcohol such as butanol (BuOH), but preferably with a greater amount of EtOH than PrOH. The present invention further relates to such a process wherein MeOH, CO, $H_2$, carbon dioxide ($CO_2$) and other carbon-containing fractions other than the primary product, are recycled into one or more of synthesis gas generation (SGG) and mixed alcohol synthesis (MAS). Yet another feature of the present invention is use of a MeOH fraction to strip out at least a portion of $CO_2$ and inert gases contained in MAS products. Finally, the present invention relates to further processing of such primary products such as exposing the primary product to a dehydration catalyst, e.g. alumina, under conditions sufficient to convert the mixture of alcohols to their corresponding olefins. If desired, the mixture of alcohols may be separated into constituent parts, e.g. EtOH, PrOH, BuOH and higher alcohols prior to dehydration.

U.S. Pat. No. 4,749,724 discloses a Fischer-Tropsch (F-T) process for making alcohols that comprises contacting a mixture of $H_2$ and CO with a catalyst comprising (1) at least one element selected from the group consisting of molybdenum (Mo), tungsten (W) and rhenium (Re) in free or combined form, (2) a promoter comprising an alkali or alkaline earth element in free or combined form, and optionally (3) a support, to form an alcohol fraction boiling in the range of motor gasoline in at least 20 percent (%) $CO_2$ free carbon selectivity. See column 4, lines 7-18, for recycling at least a portion of unconverted $H_2$ and CO contained in effluent from the process. Recycling that portion preferably occurs after removal of product alcohols, water ($H_2O$), $CO_2$ formed during the process and, even more preferably, any hydrocarbons formed during the process.

United States Patent Publication (USPP) 2005/0107482 teaches (paragraph [0006]) use of a homologation catalyst such as a cobalt/molybdenum sulfide, to homologize MeOH to EtOH in the presence of CO, optionally in the presence of one or more of $H_2$ and $CO_2$. MeOH synthesis employs a conventional catalyst such as a copper/zinc oxide catalyst. A portion of the MeOH undergoes the homologation reaction to produce EtOH while a remaining portion mixes with the EtOH to form a combined feedstream that passes to a conversion zone where it contacts a molecular sieve catalyst to produce light olefins, principally ethylene ($C_2H_6$) and propylene ($C_3H_8$).

USPP 2004/0122267 discloses a process for producing olefins that includes sequential steps of producing a MeOH stream, and passing the MeOH stream to an oxygenate conversion zone that contains a molecular sieve catalyst, especially a silicoaluminophosphates molecular sieve such as SAPO-34, to produce an olefin stream.

European Patent Publication (EP) 0 253 540 teaches preparation of a mixed alcohol product, preferably substantially free of MeOH, suitable for blending with gasoline as an octane improver. Such preparation begins with synthesis gas produced in a coal gasifier and yields raw product stream that is fractionated into a fraction containing EtOH, PrOH and BuOH and a fraction containing MeOH and involves recycling the MeOH-containing fraction. See page 4, lines 37-44, for teachings concerning recycle or discard of $CO_2$, removal of hydrocarbon gases, and recycle of unreacted synthesis gas. A liquid stream from a gas-liquid separator is passed to a fractionating column from which all the MeOH is recycled to the synthesis reactor and a mixed alcohol product containing EtOH, PrOH and BuOH is produced, possibly with small quantities of $H_2O$, See page 4, lines 12-14, for a discussion of known alcohol synthesis catalysts, such as iron oxide, copper with cobalt, and rhodium or molybdenum sulphide promoted with an alkali metal, e.g. promoted with potassium carbonate.

EP 0 311 297 discusses homologation of a lower alcohol to a higher alcohol by reacting the lower alcohol (e.g. MeOH) with synthesis gas over an alcohol synthesis catalyst and recycling the lower alcohol. Suitable synthesis catalysts include those known in the art such as iron oxide, copper with cobalt, copper promoted with potassium carbonate and rhodium or molybdenum sulphide promoted with an alkali metal such as potassium carbonate.

GB 2,185,907 teaches preparation of a promoted (e.g. with a potassium compound) $MoS_2$ catalyst and promotes its use in converting synthesis gas to alcohols containing two or more carbon atoms ($C_{2+}$).

O. I. Senol et al., "Hydrodeoxygenation of methyl esters on sulphided $NiMo/\gamma-Al_2O_3$ and $CoMo/\gamma-Al_2O_3$ catalysts", Catalysis Today 100 (2005) pages 331-335, discusses hydrodeoxygenation of one or more of carbonyl groups, carboxylic groups or methyl esters using a sulphided cobalt/molybdenum catalyst on a gamma ($\gamma$)-alumina support.

TSS Consultants, in "Gridley Ethanol Demonstration Project Utilizing Biomass Gasification Technology: Pilot Plant Gasifier and Syngas Conversion Testing", August 2002—June 2004, National Renewable Energy Laboratory (NREL) Report NREL/SR-510-37581 (February 2005) discuss conversion of rice straw to synthesis gas and use of a proprietary F-T catalyst to convert the synthesis gas to a mixture of alcohols, surplus $H_2$, methane ($CH_4$) and $CO_2$. The discussion on page 9 refers to use of a pressure swing adsorption system to remove the surplus $H_2$, $CH_4$ and $CO_2$ for recycle to appropriate points in the process. Also on page 9, the discussion addresses use of a distillation column to separate EtOH from MeOH, $H_2O$ and other (higher molecular weight) alcohols. At page 12, the discussion notes that "the nearly complete conversion of the methanol to ethanol may require recycling up to 7 or 8 times".

P. L. Spath and D. C. Dayton, in "Preliminary Screening—Technical and Economic Assessment of Synthesis Gas to Fuels and Chemicals with Emphasis on the Potential for Biomass-Derived Syngas", NREL/TP-510-34929 (December 20035) present a survey of synthesis gas production techniques as well as various processes to convert such synthesis gas to useful products. Pages 70-89 of the survey addresses synthesis of mixed higher alcohols. Synthetic routes include variants of Fischer-Tropsch Synthesis (FTS) and homologation of MeOH and lower molecular weight alcohols to make higher alcohols. At page 73, they teach that "branched higher alcohols are typically formed from modified MeOH synthesis and modified FTS catalysts and straight chain alcohols are formed when alkalized $MoS_2$ catalysts are used". They note, at page 76, that all higher alcohol synthesis (HAS) catalysts include an activating amount of an alkali metal. At page 78, they refer to 1984 vintage work by The Dow Chemical Company and Union Carbide Corporation related to supported or unsupported alkali-promoted molybdenum disulfide ($MoS_2$) or $Co/MoS_2$ catalysts. Later on the same page they teach that "adding Co to alkalized $MoS_2$ catalysts increases the production of ethanol and other higher alcohols because Co promotes the homologation of methanol to ethanol".

Claus et al., in "Selective hydrogenolysis of methyl and ethyl acetate in gas phase on copper and supported Group VIII metal catalysts", *Applied Catalysis, A: General* (1991), Volume 79(1), pages 1-18, teaches that a cobalt-rhenium-iron catalyst on a titanium dioxide support promotes formation of ethanol from ethyl acetate (EtAc).

U.S. Pat. No. 4,675,344 discloses a method for changing the ratio of MeOH to higher alcohols produced in a mixed alcohol synthesis process. The method requires adjusting a concentration of a sulfur releasing substance in a hydrogen and carbon monoxide feed. Catalysts used in the process preferably exclude Group VIII metals such as cobalt.

A first aspect of the present invention is a process for selectively producing mixed alcohols, the process comprising steps as follows:

A. generating a synthesis gas feedstock, said feedstock comprising CO and Hz;

B. contacting the synthesis gas feedstock with a mixed alcohol synthesis catalyst under conditions sufficient to produce a crude product stream;

C. effecting separation of the crude product stream into at least a first lights product stream and a heavy products stream;

D. optionally, but preferably, recycling a portion of the first lights product stream to step A or to a precursor to step A where said recycle stream combines with, respectively, synthesis gas or a precursor to synthesis gas;

E. separating the heavy products stream into at least two fractions, an ethanol-light fraction and an ethanol-heavy fraction;

F. forming a combined stream by placing at least a portion of the first lights product stream in operative contact with at least a portion of the ethanol-light fraction whereby the ethanol-light fraction functions as an absorption medium to effect absorption of at least a portion of carbon dioxide and inert gas contained in said first lights product stream;

G. optionally, but preferably, recycling at least a portion of the ethanol-light fraction to at least one of step A, step B or a precursor to step A, where said recycle stream combines with synthesis gas if it goes to step A or step B, or a precursor to synthesis gas if it goes to a precursor to step A;

H. separating the combined stream into a second lights product stream, a heavy products recycle stream, a carbon dioxide-rich recycle stream, and a purge gas fraction, the purge gas fraction comprising at least a portion of carbon dioxide and inert gases contained in the combined stream;

I. optionally, but preferably, recycling the second lights product stream to step B where said second lights product stream combines with the synthesis gas feedstock; and J. recycling the heavy products recycle stream to step E;

K. optionally recycling the carbon dioxide-rich recycle stream to step A or a precursor to step A where said recycle stream combines with, respectively, synthesis gas or a precursor to synthesis gas; and L. removing the purge gas fraction from the process for at least one of venting to the atmosphere, use as fuel gas or use in a separate process.

In a first modification, the process of the first aspect further comprises a step A', step A' being intermediate between steps A and B and comprising removing an amount of water from the synthesis gas to yield a reduced water content synthesis gas stream for step B.

A second aspect of the present invention is a process for selectively producing mixed alcohols, the process comprising steps as follows:

A. generating a synthesis gas feedstock, said feedstock comprising CO and $H_2$;

B. contacting the synthesis gas feedstock with a mixed alcohol synthesis catalyst under conditions sufficient to produce a crude product stream;

C. effecting separation of the crude product stream into at least a first lights product stream and a heavy products stream;

D. splitting the first lights product stream into a first lights product portion and a second lights product portion;

E. recycling the first lights product portion to step A or to a precursor to step A where said first lights product portion combines with, respectively, synthesis gas or a precursor to synthesis gas;

F. effecting separation of the heavy products stream into a spent gas stream and a purified heavy products stream;

G. recycling the spent gas stream to step A or to a precursor to step A where said spent gas stream combines with, respectively, synthesis gas or a precursor to synthesis gas;

H. separating the purified heavy products stream into at least two fractions, an ethanol-light fraction and an ethanol-heavy fraction;

I. recycling at least a portion of the ethanol-light fraction to at least one of step A, step B or a precursor to step A, where said recycle stream combines with synthesis gas if it goes to step A or step B, or a precursor to synthesis gas if it goes to a precursor to step A;

J. forming a combined stream by placing the first lights product portion in operative contact with at least a portion of the ethanol-light fraction whereby the ethanol-light fraction functions as an absorption medium to effect absorption of at least a portion of $CO_2$ and inert gas contained in said first lights product portion;

K. separating the combined stream into a second lights product recycle stream, a heavy products recycle stream, a carbon dioxide-rich recycle stream, and a purge gas fraction, the purge gas fraction comprising at least a portion of carbon dioxide and inert gases contained in the combined stream;

L. recycling the second lights product recycle stream to step B. where said second lights product recycle stream combines with the synthesis gas feedstock; and M. recycling the heavy products recycle stream to step H;

N. recycling the carbon dioxide-rich recycle stream to step A or a precursor to step A where said recycle stream combines with, respectively, synthesis gas or a precursor to synthesis gas; and O. removing the purge gas fraction from the process for at least one of venting to the atmosphere, use as fuel gas or use in a separate process.

In a first modification of the process of the second aspect, the process further comprises a step A', step A' preceding at least one of steps A and B and comprising removing an amount of water from at least one of synthesis gas from step A, the ethanol-light fraction from step I, the first light products portion from step E or the spent gas stream from step G, such water removal effectively providing a reduced water content synthesis gas stream for step B.

A third aspect of the present invention is a process for synthesizing a mixed alcohol product, the process comprising:

A. converting synthesis gas to a raw product stream comprising a mixed alcohol product, oxygenates and hydrocarbons other than $C_1$ to $C_5$ alcohols, unreacted synthesis gas constituents and $CO_2$, the mixed alcohol product having an ethanol content of at least 25 mole percent (mol %), preferably at least 30 mol %, more preferably at least 35 mol % and still more preferably at least 40 mol %, in each case based upon total moles of alcohol present in the mixed alcohol product;

B. recycling an amount of at least one of $CO_2$, unreacted synthesis gas constituents, MeOH and other oxygenates sufficient to provide a carbon utilization of at least 1.50 times X, preferably at least 1.55 times X, where "X" represents carbon utilization using only step A. The foregoing carbon efficiency numbers relate to synthesis gas prepared using natural gas with a methane content of 81 mol %, based upon moles of material contained in the natural gas. Skilled artisans recognize that a higher methane content should yield a higher carbon efficiency and that a methane content of less than 81 mol % necessarily leads to a downward adjustment of carbon efficiency, e.g. to at least 1.45 times X.

An aspect related to both the first and second aspects of the present invention, whether modified or not, includes subjecting the EtOH-heavy stream to dehydration conditions, including exposure to a dehydration catalyst (e.g. alumina), sufficient to convert at least EtOH to ethylene and, optionally, PrOH to propylene and, optionally, BuOH to butylene. The related aspect constitutes step M in the first aspect and step P in the second aspect. At least a portion of the raw product stream of the third aspect may also be subjected to such dehydration conditions.

If desired, the EtOH-heavy fraction is further subdivided, into a first product alcohol fraction comprising EtOH and PrOH and a second product alcohol fraction containing BuOH. This subdivision occurs subsequent to step E in the first aspect of the present invention, nominally step E', and subsequent to step H in the second aspect of the present invention, nominally step H'. Such subdivision may occur as another step in a continuous process or take place in a separate process, optionally after one or both of storage and transport to another site or location. Storage times may range from as short as several minutes to as long as several days, possibly several years. An upper limit on storage time is driven more by costs of storing a material for a prolonged period of time rather than performance of the stored material. Transport may occur by any of a number of means that include, without limit, one or more of pipelines, tank trucks, tank cars, barges, and lake or ocean-going vessels. After such subdivision, one may then subject either or both product alcohol fractions to such dehydration conditions.

Subsequent to dehydration of at least the EtOH and PrOH portions of the EtOH-heavy fraction into their corresponding light olefins, ethylene from EtOH and propylene from PrOH, a further related aspect of the present invention includes subjecting at least one olefin to polymerization conditions sufficient to form a homopolymer of a single olefin monomer, a copolymer of a single olefin monomer and a second monomer that is copolymerizable with the single olefin monomer or an interpolymer of a single olefin monomer and at least two other monomers that are copolymerizable with the single olefin monomer. Such further related aspect constitutes a sequential step N in the first aspect and a sequential step Q in the second aspect.

As used throughout this specification, definitions presented in this paragraph, in succeeding paragraphs or elsewhere in the specification, have meanings ascribed to them where first defined.

"Ethanol-light fraction" and "ethanol-heavy fraction", when used with regard to subdividing a single fraction or distillation cut, means that the EtOH-light fraction contains less EtOH than the EtOH-heavy fraction. Taken together, the EtOH-light fraction and the EtOH-heavy fraction contain substantially all and preferably all of EtOH contained in said single fraction or distillation cut. An EtOH-light fraction contains less than 50 wt % of EtOH contained in the single distillation cut, preferably less than 40 wt %, more preferably less than 30 wt %, still more preferably less than 20 wt % and even more preferably less than 10 wt %, in each case based upon total ethanol content of the single distillation cut. Conversely, the EtOH-heavy fraction contains at least 50 wt % of EtOH contained in the single distillation cut, preferably at least 60 wt %, more preferably at least 70 wt %, still more preferably at least 80 wt % and even more preferably at least 90 wt %, in each case based upon total ethanol content of the single distillation cut.

All references to Groups, e.g. Group VIII, relate to the Periodic Table of the Elements where Group VIII under a prior IUPAC format includes Groups 8, 9 and 10 in a new IUPAC format. Both formats are shown on the inside cover of *CRC Handbook of Chemistry and Physics, 77$^{th}$ Edition* (1996-1997).

When ranges are stated herein, e.g. from 2 to 10, both end points of the range (2 and 10) are included within the range unless otherwise specifically excluded.

While the description presented below addresses use of natural gas to generate synthesis gas, skilled artisans recognize that one may also generate synthesis gas using known technology such as gasifying coal or another carbonaceous material.

Figure 1:
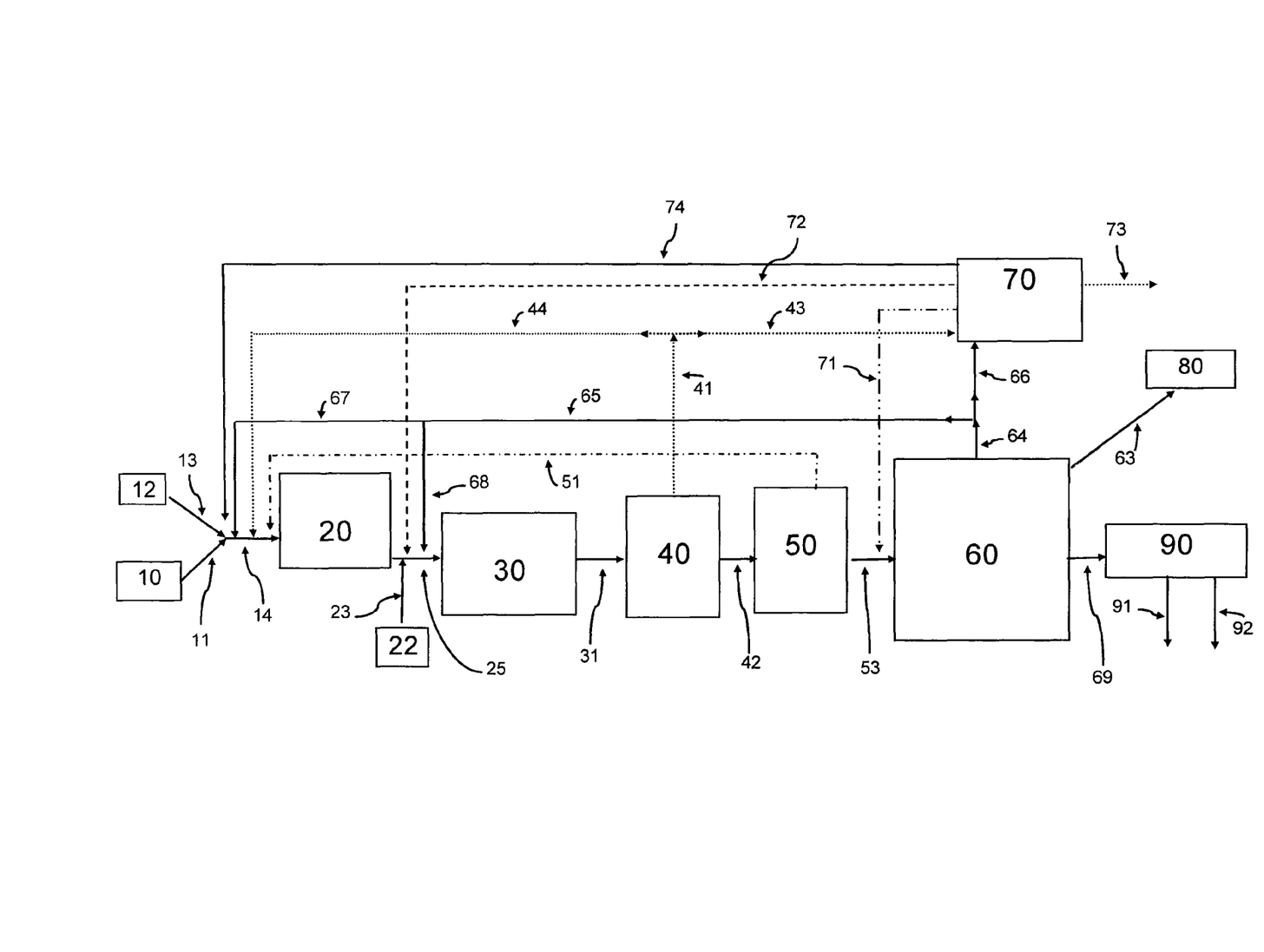
FIG. 1 is a schematic illustration of the process of the present invention.

FIG. 1 illustrates a preferred embodiment of the present invention wherein a natural gas source 10 and an oxygen ($O_2$) source 12 feed into a synthesis gas generator 20. FIG. 1 shows that natural gas from natural gas source 10 and oxygen from $O_2$ source 12 combine in a single line 14 before feeding into synthesis gas generator 20. For any of a number of reasons, one may substitute an alternate feed arrangement (not shown in FIG. 1) that eliminates line 14 and provides that each of line 11 from natural gas source 10 and line 13 from $O_2$ source 12 feed directly into synthesis gas generator 20. If one uses the alternate feed arrangement, feed from lines 44, 51, 67 and 74 can go to either of lines 11 and 13 as well as directly to synthesis gas generator 20.

A natural gas stream conveyed via a pipeline from a gas producing field serves as a preferred natural gas source 10. While all natural gas principally comprises $CH_4$, skilled artisans recognize that natural gas stream composition varies from field to field. Natural gas source 10 preferably provides a stream of natural gas that contains less than five wt % of sulfur-containing compounds, preferably less than 1 wt %, more preferably less than 0.01 wt % and most preferably less than or equal to 0.002 wt %, in each case based upon total weight of the natural gas stream. At sulfur levels of 0.01 wt % or more (e.g. 1 wt %), one or more sulfur removal techniques (e.g. adsorption beds) may be used to lower sulfur content of the natural gas. At a natural gas sulfur level of less than or equal 0.002 wt %, it is believed that the process of the present invention does not require use of sulfur removal techniques.

Air constitutes a preferred $O_2$ source 12, but skilled artisans recognize that one may also use pure or substantially pure $O_2$ if one chooses to minimize introduction of nitrogen ($N_2$) into the process or if one accepts added costs involved in purifying oxygen.

As used herein, "line" refers to a conduit, passageway, pipe, tube or other hollow body adapted for conducting a liquid, gas or finely divided solid from one location, e.g. natural gas source 10, to another, e.g. synthesis gas generator 20. For example, in FIG. 1, lines 11 and 14 effect a connection between source 10 and generator 20 and facilitate transfer of natural gas from source 10 to generator 20.

In synthesis gas generator 20, natural gas from source 10 contacts $O_2$ from source 12 under conditions effective to convert the natural gas into synthesis gas, nominally a mixture of CO, $H_2$ and, optionally, $CO_2$ and $H_2O$. Synthesis gas production processes are well known and include partial oxidation, conventional steam reforming, autothermal reforming or a combination thereof such as gas heated reforming followed by autothermal reforming. As such, synthesis gas generator 20 may be a steam reforming unit, a partial oxidation unit, an autothermal reforming unit or a combined reforming unit, e.g. a unit that combines two or more of steam reforming, partial oxidation and autothermal reforming.

When synthesis gas generator 20 is a partial oxidation unit, up to four (preferably all four) additional feedstreams enter generator 20 either directly or, preferably as shown in FIG. 1, together with $O_2$ from $O_2$ source 12 and natural gas from natural gas source 10. A first additional feedstream is a first portion of a first lights product stream from first separation unit 40. The first additional feedstream flows into generator 20, preferably via lines 41 and 44 and combined line 14. The first lights product stream comprises dissolved or unreacted CO, dissolved or unreacted $H_2$, a portion of $CO_2$ produced during mixed alcohol synthesis (MAS) in MAS generator 30, the operation of which is detailed below, a first portion of any inert gas (e.g. argon (Ar) and $N_2$) introduced into or produced by the process of the present invention, alkanes (e.g. $CH_4$, ethane ($C_2H_6$) and propane ($C_3H_8$)). A second additional feedstream is a spent gas stream that moves from second separation unit 50 to synthesis gas generator 20 via line 51 and combined line 14. A third additional feedstream is a first portion of an EtOH-light fraction (detailed below) that flows from third separation unit 60 to generator unit 20, preferably via lines 64, 65 and 67, and combined line 14. A fourth additional feedstream is a $CO_2$-rich recycle stream (detailed below) that transfers from $CO_2$ absorption and separation unit 70 to generator unit 20, preferably via line 74 and combined line 14. As noted above, skilled artisans understand that one may feed any or all of the additional feedstreams directly to generator 20 rather than via combined line 14 if one chooses to do so.

If desired, one may remove at least a portion of water contained in one or more of synthesis gas and the additional feedstreams using a water separator 20' (not shown). Water separator 20' preferably occupies a position intermediate between synthesis gas generator 20 and MAS reactor 30. When using water separator 20', a line 21 (not shown) conveys output from synthesis gas generator 20 to water separator 20' and line 25 conveys synthesis gas with a reduced water content to MAS reactor 30. An additional line 24 (not shown) conveys a stream comprising water to a site (also not shown) for further processing, re-use or disposal. One may also place water separator 20' before synthesis gas generator 20 and remove at least a portion of water from at least one of the additional streams before they enter synthesis gas generator 20.

Synthesis gas passes from synthesis gas generator 20 to MAS reactor 30 via line 25. Either separately, or preferably as a co-feed with the synthesis gas, a second portion of the EtOH-light fraction passes into MAS reactor 30 from third separation unit 60, preferably via lines 64, 65, 68 and 25. Similarly, a second lights product stream from $CO_2$ absorption and separation unit 70 passes into MAS reactor 30 either directly via line 72 or, as shown in FIG. 1, as part of a co-feed with synthesis gas via lines 72 and 25.

FIG. 1 shows a sulfur source 22 that is operatively connected to MAS reactor 30 via lines 23 and 25. Those skilled in the MAS art understand that a certain amount of a sulfur source promotes activity of certain MAS catalysts such as a preferred sulfided cobalt molybdenum catalyst (optimally activated with an alkali metal or alkaline earth metal such as potassium). When starting the process of the present invention, one may introduce a sulfur compound, such as hydrogen sulfide, into MAS reactor 30 from sulfur source 22. The amount of sulfur compound added to MAS reactor 30 from source 22 may vary based upon at least two considerations. One consideration is sulfur content of the synthesis gas which, when one generates synthesis gas from natural gas, depends upon sulfur content of the natural gas. A second consideration is sulfur content of streams that recycle to either synthesis gas generator 20 from units 40, 50, 60 and 70 or to MAS reactor 30 from units 60 and 70.

In MAS reactor 30, raw materials comprising synthesis gas from synthesis gas generator 20, the second portion of the remainder stream from unit 60, and the second lights product stream from unit 70, optionally in conjunction with an amount of a sulfur compound from sulfur source 22, contact a MAS catalyst (preferably a cobalt/molybdenum disulfide catalyst that is optionally activated with an alkali metal or alkaline earth metal and optionally supported) under conditions sufficient to convert the raw materials into a raw product stream that exits MAS reactor 30 via line 31.

First separation unit 40 partitions the raw product stream from MAS reactor 30 into a first lights product stream, a first portion of which is recycled to synthesis gas generator 20 as detailed above and a second portion of which feeds into $CO_2$ absorption and separation unit 70 via lines 41 and 43, and a heavy products stream that moves from first separation unit 40 to second separation unit 50 via line 42.

The heavy products stream comprises MeOH, EtOH, PrOH, BuOH, pentanol (PeOH), $H_2O$, esters (e.g. methyl acetate (MeAc) and ethyl acetate (EtAc)), aldehydes, $CO_2$, alkanes (e.g. $CH_4$), $N^2$, other inert gases (e.g. argon that may enter the process as a component of, respectively, air and natural gas), dissolved synthesis gas (CO and $H_2$) as well as dissolved light hydrocarbons (e.g. $CH_4$, $C_2H_6$ and $C_3H_8$). An illustrative composition for such heavy products stream is 39 mole percent (mol %) EtOH, 32 mol % MeOH, 7 mol % $CO_2$, 6 mol % PrOH, 6 mol % $H_2O$, 2 mol % $CH_4$, 2 mol % of EtAc, 1 mol % CO, 1 mol % $H_2$, 1 mol % MeAc, 1 mol % of BuOH, and 1 mol % of a combination of inert gases and materials heavier than BuOH (e.g. PeOH and waxes (also known as saturated hydrocarbons that contain less than 21 carbon atoms ($C_{21}$))).

The first lights product stream comprises CO, $H_2$, $CH_4$, $CO_2$ and inerts (e.g. $N_2$ and argon). An illustrative composition for such first lights product stream is 33 mol % $H_2$, 27 mol % CO, 19 mol % $CH_4$, 17 mol % $CO_2$, and 4 mol % inerts and other components (e.g. $N_2$, Ar and MeOH, EtOH, $C_2H_6$, esters, water, propanol and hydrocarbons), in each case based upon total moles of material contained in the first lights product stream.

Second separation unit 50 partitions the heavy products stream from first separation unit 40 into a spent gas stream that moves from unit 50 to synthesis gas generator 20 via line 51 and combined line 14 and a purified heavy stream that moves from unit 50 to third separation unit 60 via line 53. The spent gas stream comprises $CO_2$, $CH_4$, CO, $H_2$, light alcohols (e.g. MeOH and EtOH), esters, aldehydes and inert gases. An illustrative spent gas stream comprises 31 mol % $CO_2$, 17 mol % $CH_4$, 13 mol % CO, 11 mol % $H_2$, 11 mol % MeOH, 11 mol % EtOH, 2 mol % H2O, 1 mol % PrOH, 1 mol % $N_2$, 1 mol % Ar, and 1 mol % EtAc, in each case based upon total moles of material contained in the spent gas stream. The purified heavy stream comprises MeOH, EtOH, PrOH, BuOH, PeOH, esters, aldehydes, inerts (e.g. $N_2$ and Ar), $CO_2$, $H_2O$, $CH_4$, CO, and $H_2$. An illustrative purified heavy stream comprises 39 mol % EtOH, 32 mol % MeOH, 6 mol % PrOH, 7 mol % $CO_2$, 6 mol % $H_2O$, 2 mol % $CH_4$, 2 mol % EtAc, 1 mol % MeAc, 1 mol % CO, 1 mol % BuOH, 1 mol % $H_2$, and 2 mol % of a combination of inerts, aldehydes, esters, and heavier components, in each case based upon total moles of material contained in the purified heavy stream.

Third separation unit 60 partitions the purified heavy stream into at least two fractions, an EtOH-light fraction and an EtOH-heavy fraction. If desired, the purified heavy stream can be partitioned into at least three fractions including the EtOH-light fraction and the EtOH-heavy fraction as well as a LP (low pressure) gas fraction for fuel value.

The EtOH-light fraction exits unit 60 via line 64. A first portion of the EtOH-light fraction exits line 64 and transits to synthesis gas generator 20 via lines 65 and 67 and combined line 14 as well as to MAS reactor 30 via lines 65, 68 and 25. A second portion of the EtOH-light fraction exits line 64 and moves to feed into $CO_2$ absorption and separation unit 70 via line 66 for further processing.

The EtOH-heavy fraction exits unit 60 via line 69. If desired, the EtOH-heavy fraction may be further processed without an additional separation or partition step. Preferably, however, the EtOH-heavy fraction is further subdivided in fourth separation unit 90 into a first product alcohol fraction that comprises EtOH and PrOH and exits separator 90 via line 91, and a second product alcohol fraction that comprises BuOH and exits separator 90 via line 92.

When segregated or partitioned in third separation unit 60, the LP fuel gas stream exits unit 60 via line 63 for further use. Such further use may include, for example, burning as fuel or transfer to a reactor apparatus to convert one or more components of the LP fuel gas into a desired intermediate or final product.

An illustrative first product alcohol fraction comprises 75 mol % EtOH, 11 mol % water, 12 mol % PrOH, 1 mol % MeOH, and 1 mol % of a combination of butanols, esters, aldehydes and other oxygenates, in each case based upon total moles of material contained in the first product alcohol stream.

An illustrative second product alcohol fraction comprises 70 mol % BuOH, 20 mol % PeOH, 5 mol % of PrOH, and 5 mol % isobutanol (i-BuOH), in each case based upon total moles of material contained in the second product alcohol fraction.

An illustrative LP fuel gas stream comprises 63 mol % $CO_2$, 17 mol % $CH_4$, 9 mol % CO, 6 mol % $H_2$, 2 mol % MeOH, 1 mol % ethane ($C_2H_6$), 1 mol % argon (Ar) and 1 mol % of a combination of aldehydes, esters and inert materials other than Ar, in each case based upon total moles of material contained in the LP fuel gas stream.

An illustrative ethanol-light fraction comprises 85 mol % MeOH, 4 mol % EtAc, 4 mol % EtOH, 3 mol % MeAc, 1 mol % methyl propionate, 1 mol % ethyl propionate, 1 mol % ethyl aldehyde, and 1 mol % of a combination of other esters, aldehydes and inerts, in each case based upon total moles of material contained in the ethanol-light stream.

$CO_2$ absorption and separation unit 70 brings the second portion of the ethanol-light fraction into contact with the second portion of the first lights product stream (from first separation unit 40 via lines 41 and 43). The second portion of the ethanol-light fraction serves as an absorption medium that absorbs at least a portion of $CO_2$, EtOH, and heavier oxygenates (e.g. methyl acetate, ethyl acetate, propyl acetate, methyl propionate, and ethyl propionate) from the second portion of the first lights product stream.

At least a portion, preferably a significant portion, more preferably substantially all and most preferably all, of the absorbed $CO_2$ and inert gases absorbed into the second portion of the ethanol-light fraction exhausts from unit 70 via line 73 either as a vent gas, or, more preferably, as a fuel gas or as a reactant in another process. Unit 70 also separates remaining contents of the unit into the second lights product stream that recycles to MAS reactor 30 as detailed above, a predominantly $CO_2$ recycle stream that moves from unit 70 to synthesis gas generator 20 via lines 74 and 14, and a heavy products recycle stream that passes from unit 70 to the third separation unit 60, preferably via lines 71 and 53.

The predominantly $CO_2$ recycle stream that transits to synthesis gas generator 20 preferably comprises $CO_2$, $CH_4$, $C_2H_6$, MeOH and unreacted synthesis gas components (principally CO and $H_2$). An illustrative predominantly $CO_2$ recycle stream comprises 85 mol % $CO_2$, 7 mol % $CH_4$, 2 mol % CO, 2 mol % MeOH, 1 mol % $C_2H_6$ and 1 mol % $H_2$ with the rest are made up of mainly by MeAc, EtAc, pentane, $C_2H_{18}$ and inert gas in each case based upon total moles of material contained in predominantly $CO_2$ recycle stream.

The second lights product stream preferably comprises $H_2$, CO, $CH_4$, $CO_2$, and inert materials. An illustrative second light product recycle stream contains 41 mol % $H_2$, 33 mol % CO, 20 mol % $CH_4$, 3 mol % $CO_2$, 2 mol % $N^2$, and 1 mol % Ar, in each case based upon total moles of material contained in the second light product stream.

The heavy products recycle stream preferably comprises MeOH, EtOH, EtAc, $H_2O$, $CO_2$, PrOH, MeAc, methyl propionate, ethyl propionate, and other oxygenates (e.g. propyl acetate, methyl butyrate, ethyl butyrate, and propyl propionate). An illustrative heavy product recycle stream contains 64 mol % MeOH, 21 mol % EtOH, 4 mol % EtAc, 3 mol % $H_2O$, 2 mol % $CO_2$, 2 mol % PrOH, 1 mol % MeAc, 1 mol % methyl propionate, 1 mol % ethyl propionate and 1 mol % of a combination of other esters, aldehydes and other oxygenates, in each case based upon total moles of material contained in the heavy products recycle stream.

As the process illustrated in FIG. 1 and described in detail above is preferably a continuous process, several of the steps occur concurrently or substantially so once an initial aliquot of synthesis gas passes through the entire process.

Beginning with that initial aliquot, natural gas from source 10 and oxygen-containing gas from source 12 flow simultaneously, via respective lines 11 and 13, into combined line 14, and from line 14 into synthesis gas generator 20. Synthesis gas generator 20, in turn, converts the natural gas and oxygen-containing gas into synthesis gas.

The synthesis gas transits from generator 20 to MAS reactor 30 via line 25. A co-feed of a sulfur-containing material from sulfur source 22, when needed, enters MAS reactor 30 concurrently with the synthesis gas via lines 23 and 25. MAS reactor 30 contains a MAS catalyst that, when assisted by the sulfur-containing material, converts synthesis gas into a crude product stream.

The crude product stream flows from MAS reactor 30 to the first separation unit 40 via line 31. First separation unit 40 splits the crude product stream into a first lights product stream and a heavy products stream. The first lights product stream exits unit 40 via line 41 at the same time the heavy products stream exits unit 40 via line 42. The first lights product stream splits into two fractions, a first lights product portion and a second lights product portion by way of a flow diverter such as a T-connector. The first lights product portion flows from line 41 through line 44 either directly into synthesis gas generator 20 or, as shown in FIG. 1, indirectly into generator 20 via line 44 and combined line 14 as a co-flow with the natural gas and oxygen-containing gas. At the same time, the second lights product portion flows from line 41 to $CO_2$ absorption and separation unit 70 via line 43.

An optional, but preferred, separation of the heavy products stream occurs in second separation unit 50. Second separation unit 50 splits the heavy products stream into a spent gas stream and a purified heavy products stream. Simultaneously, the spent gas stream flows from second separation unit 50 via line 51 to synthesis gas generator either directly (not shown) or as illustrated in FIG. 1 via line 51 and combined line 14 and the purified heavy products stream flows to third separation unit 60 via line 53. The spent gas stream effectively flows concurrently with natural gas and the oxygen-containing gas into generator 20 via combined line 14.

Third separation unit 60 splits the purified heavy products stream into at least two, preferably at least three fractions. In either case, two fractions are an EtOH-light fraction and an EtOH-heavy fraction. When splitting into three fractions, the third fraction is an LP gas fraction or stream. The fractions, whether two, three or more than three, flow simultaneously from third separation unit 60. The EtOH-heavy fraction exits unit 60 via line 69 while the EtOH-light fraction flows from unit 60 via line 64 and, when separating a third fraction, the LP gas fraction flows from unit 60 via line 63. The EtOH-heavy fraction desirably has an ethanol content of at least 25 mole percent (mol %), preferably at least 30 mol %, more preferably at least 35 mol % and still more preferably at least 40 mol %, in each case based upon total moles of alcohol present in the EtOH-heavy fraction.

The EtOH-heavy fraction may be subjected to further processing, e.g. processing under dehydration conditions, either as is or following segregation into at least a first product alcohol fraction comprising EtOH and PrOH and a second product alcohol fraction comprising BuOH. The dehydration conditions are sufficient to convert at least EtOH to ethylene, PrOH to propylene and, optionally, BuOH to butylene. Separation may occur, as shown in FIG. 1, via a fourth separation unit 90, with the first product alcohol fraction and second product alcohol fraction simultaneously exiting unit 90, the first product alcohol fraction via line 91 and the second product alcohol fraction via line 92.

One or more of ethylene, propylene and butylenes may be subjected to conditions sufficient to form a homopolymer of a single olefin monomer (e.g. ethylene, propylene or butylenes), a copolymer of a single olefin monomer and a second monomer that is copolymerizable with the single olefin monomer (e.g. a copolymer of ethylene as the single olefin monomer and propylene as the second or copolymerizable monomer or a copolymer of ethylene as the single olefin monomer and octene as the second or copolymerizable monomer), or an interpolymer of a single olefin monomer and at least two other monomers that are copolymerizable with the single monomer (e.g. an interpolymer of ethylene as the single olefin monomer, propylene and a diene monomer as the other two monomers).

The EtOH-light fraction preferably splits into two simultaneous flow portions. One flow portion passes from line 64 into line 66 and then into $CO_2$ absorption and separation unit 70. The second flow portion passes to at least one, preferably both, of a feed into synthesis gas generator 20 (preferably via lines 65 and 67 and combined line 14) and a feed into MAS reactor 30 (preferably via lines 65, 68 and 25).

$CO_2$ absorption and separation unit 70 effectively forms a combined stream by placing the first lights product fraction that enters unit 70 from first separation unit 40 via lines 41 and 43 in operative contact with at least part of the second flow portion of the EtOH-light fraction, whereby the EtOH-light fraction functions as an absorption medium that effects absorption of at least a portion of $CO_2$ and inert gas (e.g. Ar) contained in the first lights product fraction. $CO_2$ absorption and separation unit 70 also effects separation of the combined stream into at least four substreams, all of which simultaneously flow from unit 70.

One stream is a $CO_2$-rich recycle stream that flows from unit 70 via line 74 either directly (not shown) or indirectly (shown in FIG. 1) to synthesis gas generator 20. The indirect flow occurs via line 74 and combined line 14 such that second lights product stream co-flows with the oxygen-containing gas from oxygen source 12 and natural gas from natural gas source 10.

A second stream is a heavy products recycle stream that flows from unit 70 to third separation unit 60 either directly (not shown) or indirectly via lines 71 and 53. In the indirect flow, heavy products recycle stream co-flows into third separation unit 60 with the purified heavy products stream.

A third stream is a second lights product stream that flows from unit 70 to MAS reactor 30 either directly (not shown) or indirectly (shown in FIG. 1) via lines 72 and 25. With the indirect flow, the second lights product stream co-flows into MAS reactor 30 with synthesis gas from synthesis gas generator 20.

A fourth stream is a purge gas fraction that flows from $CO_2$ absorption and separation unit 70 via line 73. By extracting the purge gas fraction from process flows, it is believed that one is able to substantially maintain use of a constant portion of reactor volume in MAS reactor 30. Absent such extraction, it is believed that $CO_2$ and inert gases would, upon being recycled, form an ever-increasing fraction of material flowing into MAS reactor 30, thereby decreasing reaction rate or requiring either larger MAS reactors or multiple MAS reactors.

The third aspect of the present invention includes a step of recycling an amount of at least one of $CO_2$, unreacted synthesis gas constituents, MeOH and other oxygenates sufficient to provide a carbon utilization of at least 1.50 times X, preferably at least 1.55 times X, where "X" represents carbon utilization using only step A. The foregoing carbon utilization numbers relate to synthesis gas prepared using natural gas with a methane content of 81 mol %, based upon moles of material contained in the natural gas. Skilled artisans recognize that a higher methane content should yield a higher carbon efficiency and that a methane content of less than 81 mol % necessarily leads to a downward adjustment of carbon utilization, e.g. to at least 1.45 times X.

A dimethyl ether of polyethylene glycol (SELEXOL™, The Dow Chemical Company) may be used for gas treatment in high-pressure, low-temperature, high-acid gas systems. A known use for SELEXOL solvents is bulk removal of $CO_2$ from a gaseous stream.

Various amines (marketed under the trade name UCAR-SOL™, The Dow Chemical Company) may be used for gas treatment in high-pressure, low-temperature, high-acid gas systems. A known use for UCARSOL solvents is bulk removal of $H_2S$ and/or $CO_2$ from a gaseous stream.

UOP LLC markets a thermally regenerated cyclical solvent process under the trade name BENFIELD™. The process uses an activated, inhibited hot potassium carbonate solution to remove $CO_2$, hydrogen sulfide ($H_2S$) and other acid gas components that may be present in, for example, natural gas.

J. Tim Cullinane and Gary T. Rochelle, Department of Chemical Engineering, The University of Texas at Austin discuss $CO_2$ absorption in "Carbon dioxide absorption with aqueous potassium carbonate promoted by piperazine", *Chemical Engineering Science* 59 (2004), pages 3619-3630. They conclude that piperazine is an effective promoter of $CO_2$ absorption in aqueous potassium carbonate and may lower energy costs associated with $CO_2$ removal.

H. Weiss teaches, in "Rectisol wash for purification of partial oxidation gases", *Gas Separation & Purification,* 1988 Volume 2, December, pages 171-176, that "chemical and physical wash processes are the two principal methods used for removing $CO_2$, $H_2S$ and COS (carbonyl sulfide) from a gas mixture". See page 171. The RECTISOL™ process (Linde Aktiengesellschaft) uses methanol as a wash solvent.

A. Kohl and F. Riesenfeld discuss other solvents used in removing $H_2S$ and $CO_2$ from gaseous streams in their book entitled *Gas Purification,* $4^{th}$ ed., Gulf Publishing Co., 1985. These alternative solvents include but are not limited to water, ammonia, propylene carbonate, and N-methyl-2-Pyrrolidone.

D. I. Kebek, E. Polla and F. P. Wilcher of UOP LLC discuss three gas separation and purification schemes in "Purification and Recovery Options for Gasification", Form No: 170-01448-0904. The schemes include the SELEXOL™ process for acid gas removal, the POLYSEP™ membrane and the POLYBED™ pressure swing absorption (PSA) system. In an integrated Gasification Combined Cycle (IGCC), they teach sulfur removal via COS hydrolysis to convert COS to $H_2S$ and $CO_2$ combined with selective $H_2S$ removal using a SELEXOL unit. They note that one can $H_2$-enrich a portion of a SELEXOL synthesis gas product using a POLYSEP membrane and then use a POLYBED PSA unit to yield a high-purity $H_2$ stream. The POLYSEP membrane technology employs a polymer packaged as a hollow fiber in combination with a pressure differential that is established across the membrane. Molecules that permeate quickly, such as H2 and CO2, can be separated from molecules that permeate more slowly such as CO, $CH_4$ and $N_2$. POLYBED PSA systems operate by adsorbing light gases, such as CO, $CO_2$ and $CH_4$ from $H_2$-containing feed streams onto a fixed bed of adsorbents. As $H_2$ adsorbs into the bed only in small amounts, it can be recovered at a relatively high pressure and purity after passing through the bed. Bed regeneration involves reducing pressure on the adsorbent bed to allow impurities to desorb from adsorbent particles.

U.S. Pat. No. 4,752,622 discusses a process for making an alcohol fraction boiling in the range of motor gasoline. The process comprises contacting a mixture of $H_2$ and CO with a catalyst comprising a first component, a second component, a third component and, optionally, a fourth component. The first component is selected from Mo and W in free or combined form. The second component is selected from iron (Fe), Co and nickel (Ni) in free or combined form. The third component is a promoter comprising an alkali metal or an alkaline earth metal in free or combined form. The fourth component is a support.

U.S. Pat. No. 4,752,623, which stems from the same original application as U.S. Pat. No. 4,752,622, provides various techniques for preparing the catalyst used in U.S. Pat. No. 4,752,622.

U.S. Pat. No. 4,825,013 discloses a modification of the process of U.S. Pat. No. 4,752,622. The modification involves adding a lower alcohol to the mixture of $H_2$ and CO. Doing so apparently leads to homologation of the lower alkanol. According to column 3, lines 6-7, preferred lower alcohols contain from one to five carbon atoms ($C_1$-$C_5$). The lower alcohol is more preferably a $C_1$-$C_3$ alcohol with MeOH being most preferred. U.S. Pat. No. 4,825,013 teaches, at column 3, lines 22-24, fractionating a mixed alcohol fraction to remove the MeOH and then recycling the MeOH back into the mixture of $H_2$ and CO. The examples show production of small amounts of esters, specifically MeAc and EtAc, relative to alcohol production, especially MeOH and EtOH which are, respectively, the largest and second largest oxygenate fractions in the product.

The teachings of U.S. Pat. Nos. 4,752,622, 4,752,623 and 4,825,013 are incorporated herein to the maximum extent permitted by law.

U.S. Pat. No. 4,749,724, the relevant teachings of which are incorporated herein to the maximum extent permitted by law, discloses (column 3, lines 4-18) that synthesis gas (also known as syngas) production may take place via any of a number of known procedures. Illustrative procedures include gasification of hydrocarbonaceous materials such as coal, high specific gravity oils, or natural gas; partial combustion cracking of hydrocarbons; steam reforming of liquid or gaseous hydrocarbons; the water gas shift reaction; or some combination of these. The two components (CO and $H_2$) may also be generated separately and CO in the feed gas which contacts the catalyst ranges generally from 0.25 to 100, preferably from 0.5 to 5 and more preferably from 0.7 to 3. A most preferred range is from 0.7 to 1.5. While the above description focuses upon using natural gas as a feedstock to generate syngas by one or more of partial oxidation, steam reforming and autothermal reforming, syngas production may occur via any of the techniques disclosed in U.S. Pat. No. 4,749,724 without departing from the scope of the present invention.

Patent Cooperation Treaty published application WO 01/44145 relates to a process for producing olefins, especially alpha ($\alpha$)-olefins. The process includes a first step that oxidizes paraffin to alcohol and a second step of dehydrating the alcohol to give an olefin. Pages 3 and 4 include a summary of known teachings relative to alcohol dehydration. For example, alcohol dehydration typically occurs at atmospheric pressure and at a temperature of between 100° C. and 350° C. to yield an olefin and water. Typical dehydration catalysts include aluminum oxide ($Al_2O_3$), zeolites, magnesium sulfide, a combination of titanium dioxide ($TiO_2$) and $Al_2O_3$, $Al_2O_3$ modified with sodium (Na), and zirconium oxide. Dehydration catalysts preferred for use in the second step preferably include Al2O3-supported zirconium oxide catalysts, with gamma ($\gamma$)-$Al_2O_3$ and theta ($\theta$)-$Al_2O_3$ being preferred for the support.

U.S. Pat. No. 4,762,858, the relevant teachings of which are incorporated herein to the maximum extent permitted by law, discloses alcohol synthesis procedures at column 10, line 5 through column 11, line 28. Such teachings specify molar ratios of $H_2$ to CO in synthesis gas, operating pressures, temperatures, gas hourly space velocity (GHSV) of synthesis gas feed, and recycle ratio.

The molar ratio of $H_2$ to CO in syngas can vary over a broad range that favors production of oxygenated hydrocarbons. Preferable lower limits of the ratio are about 0.2, more preferably about 0.25, most preferably about 0.5 and especially about 0.7. Equivalent preferable upper limits are about 100, more preferably about 5, most preferably about 3 and especially about 1.5.

Operating pressures include pressures of 150 pounds per square inch gauge (psig) (1.05 megapascals (MPa)) or greater, with pressures in excess of 500 psig (3.55 MPa) being preferred and pressures in excess of 750 psig (5.2 MPa) being more preferred. An especially preferred pressure lies within a range of from 1,500 psig (10.3 MPa) to 4,000 psig (27.6 MPa). Pressures in excess of 4,000 psig (27.6 MPa), while possible tend to be economically unattractive due to cost of high pressure vessels, compressors and energy costs. With that in mind, one can go as high as 20,000 psig (137.9 MPa), but a pressure of 10,000 psig (68.9 MPa) or less is more preferred and a pressure of 5,000 psig (34.56 MPa) is still more preferred and a pressure of about 2000 psig (13.8 MPa) to 3,000 psig (20.7 MPa) provides very satisfactory results.

Alcohol synthesis temperatures are desirably at least 200° C. and preferably at least 220° C., but less than or equal to 500° C., preferably less than 400° C., more preferably less than 350° C. An especially preferred temperature lies within a range of from 300° C. to 350° C.

The GHSV of the synthesis gas feed is such that the C.sub.1-10 oxygenated hydrocarbons are produced and may vary over a very wide range, as is known in the art, preferably from about 50 hour$^{-1}$ to about 20,000 hour$^{-1}$. More preferably, lower limits of GHSV are about 200 hour$^{-1}$, most preferably about 300 hour$^{-1}$. Also, more preferable upper limits of GHSV are about 10,000 hour$^{-1}$ and most preferably about 5,000 hour$^{-1}$. Within the preferred ranges, conversion usually decreases as GHSV increases. Concurrently, however, productivity usually increases. Productivity may be measured by mass of product produced per unit volume of catalyst.

Preferably, the co-products formed with the alcohol fraction in the mixed alcohols process are primarily gaseous products. That is, they are preferably primarily $C_{1-4}$ hydrocarbons. Preferably, $C_{5+}$ hydrocarbons are co-produced therein at less than about 20 percent $CO_2$-free carbon selectivity, more preferably at less than 10 percent and most preferably at less than 5 percent. Lower amounts of normally liquid hydrocarbons make the normally liquid alcohols easier to separate from by-products.

Under preferred conditions, the amount of water ($H_2O$) formed is substantially less than the amount of desired product formed. Preferably, there is less than 20 wt % and more preferably less than 15 wt % $H_2O$ based on the quantity of desired oxygenated product, especially wherein the desired product is $C_{1-10}$ more especially $C_{1-5}$ and most especially $C_{2-5}$ mixed alcohols.

Analytical Procedures

Use an Agilent HP 5890 Series II Gas Chromatograph (GC) configured for on-line analysis to determine composition of material contained in each of the lines shown in FIG. 1. The GC configuration uses three columns: a 25 meter (m) by (x) 0.53 millimeter (mm) inner diameter (I.D.) PoraBOND Q (Varian CP7354); a 25 m×0.32 mm I.D. PoraPLOT U (Varian CP758115); and a 10 m×0.32 mm MS-5A (Varian CP7535). The GC configuration also includes both a flame ionization detector (FID) and a thermal conductivity detector (TCD).

Place the MS-5A and PoraPLOT U columns in a column reversal configuration using a Valco 6 port valve (Valco A4C6UWP) and connect them to the TCD. Connect the PoraBOND Q to the FID. This configuration takes advantage of a simultaneous injection onto both column sets to allow for quantization of 30 different components including inert gases and hydrocarbons.

Use a block and bleed heated gas sampling system to deliver a single phase vapor sample from the reactor outlet to the GC. Use a Valco 6-port multi-position valve to convey a select stream from a line to the GC.

Calibrate the GC using an external standard calibration. The external standard calibration determines a response factor (RF) for each individual component by analyzing either a certified gas standard or a gas mix created by injecting each liquid component into a 3 liter Tedlar™ bag and quantitatively diluting the component with nitrogen. Calculate a RF for each component by dividing concentration of the component (either in the certified gas standard or the gas mix, whichever is appropriate) by its corresponding GC peak area for each component in the standard. Determine reactor stream composition by multiplying peak area for each measured sample stream component by its corresponding calculated RF. A typical limit of detection (LOD) for each component measured using FID is 6 parts per million parts by volume (ppm(v)) and a typical limit of quantization (LOQ) for each component is 20 ppm(v). The relative precision of the GC method is +/−2% for each component.

The following examples illustrate, but do not limit, the present invention. All parts and percentages are based upon weight, unless otherwise stated. All temperatures are in ° C. Examples (Ex) of the present invention are designated by Arabic numerals and Comparative Examples (Comp Ex) are designated by capital alphabetic letters. Unless otherwise stated herein, "room temperature" and "ambient temperature" are nominally 25° C.

EX 1

As a reactor chamber use a fourteen (14) inch (35.6 centimeter (cm)) length of stainless steel tubing that has an outer diameter (O.D.) of one-quarter inch (¼") and a wall thickness of 0.035" (0.89 millimeter (mm)).

Crush pellets (cylinders having a diameter of ⅛" (0.3 cm) and a length of 3/16" (0.5 cm)) of a potassium-modified cobalt molybdenum disulfide catalyst compounded with a clay binder (66 wt % $CoMo_2S_x$ (x may vary between 4 and 6, with an average value being 5) powder, 20 wt % Bentonite L clay (Southern Clay Products), 10 wt % potassium carbonate ($K_2CO_3$) and 4 wt % of a lubricant (a powdered, hydrogenated food grade oil, e.g. STEREOTEX™ NF, ABITEC Corporation), in each case based upon pellet weight) prepared and supplied by Sud Chemie into particles having a size range of from 20 mesh (US mesh equivalent to 850 micrometer (μm) screen opening) to 40 mesh (US mesh equivalent to 425 um screen opening). Into the reactor chamber, place six milliliters (ml) of the crushed pellets and an amount of inert quartz chips having a size range of from 20 mesh US mesh equivalent to 850 um screen opening) to 40 mesh (US mesh equivalent to 425 μm screen opening) sufficient to fill the chamber.

Introduce a combined feed stream to the reactor chamber using sequential steps as follows. First, mix hydrogen sulfide ($H_2S$) into $H_2$ in an amount of 2500 parts by volume of $H_2S$ per million parts by volume of $H_2$. Using a mass flow controller, feed the gas mixture and a second gas at a volume ratio of 0.4:20 to the reactor chamber. The second gas contains 47.5 volume percent (vol %) $H_2$, 47.5 vol % CO and 5 vol % $N_2$.

Use fluidized sand to heat the reactor chamber and its contents to temperatures shown in Table 1.

When adding MeOH to the reactor chamber, use a liquid syringe pump to feed MeOH to a vaporizer where it admixes with the combined feedstream before the combined feedstream enters the reactor chamber. Adjust MeOH feed rate to the reactor so that it matches reactor effluent MeOH content to simulate steady state operating conditions (i.e. no net MeOH production).

Determine vapor phase product reactor composition via GC analysis as detailed above. Product EtOH content (wt %) equals 100 times the quotient of weight of ethanol in product divided by total weight of alcohol in the product.

Table 1 below summarizes process conditions and various product parameter for Case A (no MeOH feed) and Case B (MeOH fed at a rate of 8 pounds per cubic foot per hour (lb/ft$^3$/hr) (128.1 kilograms per hour per cubic meter (kg/hr/m$^3$). Case B represents the present invention.

Determine CO conversion by a formula wherein CO conversion=a quotient of a numerator that is a difference between CO content in feed to MAS reactor 30 and CO content in raw product that exits MAS reactor 30 and a denominator that is CO content in feed to MAS reactor 30. GC analysis provides such CO contents.

Hydrocarbon (HC) selectivity equals (=) 100 times a quotient determined by dividing (a) moles of carbon contained in methane and ethane in the gas used to prepare a mixture of CO and H$_2$ by (b) a difference determined by subtracting moles of CO$_2$ in product gases from moles of CO converted to product gases.

Determine alcohol (e.g. EtOH or PrOH) selectivity using the formula for HC selectivity, but substituting moles of carbon contained in product EtOH or product PrOH, whichever is appropriate, for (a). Determine MeOH selectivity in the same manner where no MeOH is added to the process. With a balancing of MeOH feed to equal MeOH production, net MeOH equals zero and MeOH selectivity need not be determined.

For the process of the present invention as schematically illustrated in FIG. 1 and as explained in detail above, carbon contained in, for example, natural gas that does not yield desired products such as EtOH and PrOH in a first pass through MAS reactor 30 may do so when it re-enters MAS reactor 30 either directly from, for example either or both of third separation unit 60 and CO$_2$ absorption and separation unit 70, or indirectly via synthesis gas generator 20 when contents of, for example, line 64, 65 and 67 from third separation unit 60 flow into synthesis gas generator 20. As such carbon has more than one chance to result in a desired product, a factor denominated as "Carbon Utilization", sometimes alternately referred to as "carbon efficiency", provides a measure of effectiveness of the process of the present invention. Carbon Utilization or "CU" equals a quotient of a numerator that is a sum of moles of carbon in EtOH product plus moles of carbon in PrOH product and a denominator that equals number of moles of carbon in carbon-containing materials fed that enter synthesis gas generator 20 (e.g. moles of carbon in natural gas that enters synthesis gas generator 20 through line 11). In other words, it is a measure of how much of the carbon that is fed into synthesis gas generator 20 results in desired products, in this case EtOH and PrOH. One can easily modify the numerator to add other oxygenates such as BuOH if such other oxygenates fall into a class of desired products.

In a single pass experiment, such as that illustrated in Table 1 below, the quotient labeled as "Carbon Utilization" is relabeled as "Hydrocarbon Selectivity" or "HC Selectivity". Because carbon entering a synthesis gas reactor in a single pass experiment has only one opportunity to yield a desired product such as EtOH and PrOH, skilled artisans readily recognize that HC selectivity for a natural gas feed is necessarily lower than Carbon Utilization for the same natural gas feed as Carbon Utilization factors in multiple carbon conversion opportunities.

Abbreviations used in Table 1 and their associated meanings include:

Temp=temperature

PSIA=pounds per square inch absolute

MPa=megapascals

SCCM=standard cubic centimeters per minute

GHSV=gas hourly space velocity

TABLE 1

| Parameter | Case A | Case B |
|---|---|---|
| Temp (° C.) | 319.8 | 320.0 |
| Pressure (psia/MPa) | 2998.2/20.7 | 2923.4/20.2 |
| Flow (sccm) | 200.9 | 301.2 |
| GHSV (hr$^{-1}$) | 3009 | 3012 |
| CO conversion (%) | 41.1 | 53.7 |
| HC Selectivity | 16.3 | 24 |
| MeOH Productivity (lb/ft$^3$/hr)/Metric equivalent | 8.2/ | 0 |
| EtOH Productivity (lb/ft$^3$/hr)/Metric equivalent | 11.7/ | 15.7/ |
| PrOH Productivity (lb/ft$^3$/hr)/Metric equivalent | 2.2/ | 2.4/ |
| Product Ethanol Content (wt %) | 51.6 | 58.7 |

The data presented in Table 1 demonstrate that achieving a state of no net MeOH production is possible. The data also demonstrate that addition of MeOH improves yield of product EtOH. Of equal, if not greater importance, however, the data in Table 1 provide a basis for simulating the process of the present invention as explained below.

Use the data in Table 1 to build a simulation in ASPEN-PLUS™, version 12.1 for a process that produces alcohols higher than MeOH and includes use of MeOH to remove a portion of CO$_2$ contained in effluent from a MAS reactor as well as recycle of MeOH to both a synthesis gas reactor (nominally block 20 in FIG. 1) and a MAS reactor (nominally block 30 in FIG. 1). It is believed that a skilled artisan can easily replicate the simulation using the same software and a personal computer. Similar results may be obtained with other process flow sheet simulation software.

Tables 2A through 2C summarize ASPEN simulation data for the process illustrated in FIG. 1. Each of the columns headed by a number, e.g. 11, relates to a line in FIG. 1. For example, data below 11 shows composition of the natural gas source and data below 13 shows composition of the oxygen source. Table 3 collects flow rate, in kilograms per hour (kg/hr), temperature (degrees centigrade (° C.), and pressure (bar/megapascals (MPa)) data for streams present in each of the lines shown in Table 1.

The process illustrated in FIG. 1 provides for purging a portion of CO$_2$ and inert gases from the process. By way of contrast, eliminating the CO$_2$ and inert gas purge leads to accumulation of such gases with consequent decrease in capacity in, for example, MAS reactor 30. An additional challenge that follows from failure to purge CO$_2$ and inert gases is an inability to reach steady state operations.

TABLE 2A

| Component (mole fraction) | Line No | | | | | | |
|---|---|---|---|---|---|---|---|
| | 11 | 13 | 23 | 25 | 31 | 41, 43 & 44 | 42 |
| $N_2$ | 5.12E−03 | 0.00E+00 | 0.00E+00 | 1.16E−02 | 1.51E−02 | 1.69E−02 | 7.90E−04 |
| $O_2$ | 0.00E+00 | 9.95E−01 | 0.00E+00 | 1.17E−14 | 1.52E−14 | 1.71E−14 | 1.23E−15 |
| Ar | 0.00E+00 | 5.00E−03 | 0.00E+00 | 7.11E−03 | 9.28E−03 | 1.04E−02 | 7.80E−04 |
| $H_2O$ | 0.00E+00 | 0.00E+00 | 0.00E+00 | 1.57E−03 | 7.02E−03 | 4.74E−03 | 5.76E−02 |
| $H_2$ | 0.00E+00 | 0.00E+00 | 0.00E+00 | 4.35E−01 | 2.90E−01 | 3.26E−01 | 1.07E−02 |
| CO | 0.00E+00 | 0.00E+00 | 0.00E+00 | 3.96E−01 | 2.40E−01 | 2.69E−01 | 1.48E−02 |
| $CO_2$ | 1.13E−02 | 0.00E+00 | 0.00E+00 | 4.35E−02 | 1.61E−01 | 1.72E−01 | 7.23E−02 |
| $CH_4$ | 8.16E−01 | 0.00E+00 | 0.00E+00 | 1.04E−01 | 1.71E−01 | 1.90E−01 | 2.36E−02 |
| $C_2H_6$ | 7.78E−02 | 0.00E+00 | 0.00E+00 | 5.07E−04 | 1.90E−03 | 2.06E−03 | 6.49E−04 |
| $C_3H_8$ | 0.00E+00 | 0.00E+00 | 0.00E+00 | 3.47E−05 | 2.82E−04 | 2.98E−04 | 1.58E−04 |
| 1,5-Hexadiene | 2.86E−02 | 0.00E+00 | 0.00E+00 | 0.00E+00 | 0.00E+00 | 0.00E+00 | 0.00E+00 |
| N-Butane | 2.77E−02 | 0.00E+00 | 0.00E+00 | 1.85E−07 | 1.98E−05 | 1.98E−05 | 1.97E−05 |
| N-Pentane | 3.38E−02 | 0.00E+00 | 0.00E+00 | 7.55E−06 | 2.41E−04 | 2.28E−04 | 3.37E−04 |
| N-Hexane | 0.00E+00 | 0.00E+00 | 0.00E+00 | 1.86E−06 | 9.18E−06 | 7.46E−06 | 2.25E−05 |
| Formaldehyde | 0.00E+00 | 0.00E+00 | 0.00E+00 | 5.19E−06 | 6.77E−06 | 2.75E−08 | 5.89E−05 |
| Acetaldehyde | 0.00E+00 | 0.00E+00 | 0.00E+00 | 5.88E−06 | 3.72E−05 | 8.92E−05 | 2.55E−03 |
| N-Propionaldehyde | 0.00E+00 | 0.00E+00 | 0.00E+00 | 2.22E−06 | 1.14E−04 | 2.12E−05 | 8.28E−04 |
| Dimethyl Ether | 0.00E+00 | 0.00E+00 | 0.00E+00 | 6.28E−07 | 3.57E−05 | 2.78E−05 | 9.66E−05 |
| MeOH | 0.00E+00 | 0.00E+00 | 0.00E+00 | 3.43E−04 | 4.09E−02 | 4.93E−03 | 3.19E−01 |
| EtOH | 0.00E+00 | 0.00E+00 | 0.00E+00 | 5.11E−06 | 4.77E−02 | 3.67E−03 | 3.88E−01 |
| PrOH | 0.00E+00 | 0.00E+00 | 0.00E+00 | 1.46E−06 | 7.06E−03 | 3.03E−04 | 5.93E−02 |
| Isopropanol | 0.00E+00 | 0.00E+00 | 0.00E+00 | 6.14E−08 | 1.68E−04 | 1.04E−05 | 1.38E−03 |
| N-Butanol | 0.00E+00 | 0.00E+00 | 0.00E+00 | 1.49E−08 | 7.52E−04 | 1.48E−05 | 6.45E−03 |
| Isobutanol | 0.00E+00 | 0.00E+00 | 0.00E+00 | 1.32E−08 | 2.21E−04 | 6.72E−06 | 1.88E−03 |
| 1-Pentanol | 0.00E+00 | 0.00E+00 | 0.00E+00 | 6.86E−10 | 1.39E−06 | 1.68E−06 | 1.20E−03 |
| Formic Acid | 0.00E+00 | 0.00E+00 | 0.00E+00 | 1.04E−06 | 1.36E−06 | 8.51E−08 | 1.12E−05 |
| Propionic Acid | 0.00E+00 | 0.00E+00 | 0.00E+00 | 7.66E−14 | 1.00E−13 | 6.22E−16 | 8.68E−13 |
| Acetone | 0.00E+00 | 0.00E+00 | 0.00E+00 | 1.81E−06 | 9.04E−05 | 2.44E−05 | 6.00E−04 |
| Methyl Ethyl Ketone | 0.00E+00 | 0.00E+00 | 0.00E+00 | 5.52E−07 | 3.01E−05 | 5.37E−06 | 2.21E−04 |
| Methyl Formate | 0.00E+00 | 0.00E+00 | 0.00E+00 | 2.67E−06 | 1.42E−04 | 8.71E−05 | 5.70E−04 |
| Methyl Acetate | 0.00E+00 | 0.00E+00 | 0.00E+00 | 3.25E−05 | 1.59E−03 | 5.06E−04 | 1.00E−02 |
| Ethyl Acetate | 0.00E+00 | 0.00E+00 | 0.00E+00 | 4.96E−05 | 2.26E−03 | 5.45E−04 | 1.55E−02 |
| Methyl Propionate | 0.00E+00 | 0.00E+00 | 0.00E+00 | 2.53E−05 | 6.77E−04 | 1.59E−04 | 4.67E−03 |
| Ethyl Propionate | 0.00E+00 | 0.00E+00 | 0.00E+00 | 2.65E−05 | 4.35E−04 | 1.18E−04 | 2.88E−03 |
| Propyl Acetate | 0.00E+00 | 0.00E+00 | 0.00E+00 | 3.38E−06 | 2.30E−04 | 3.75E−05 | 1.72E−03 |
| Methyl Butyrate | 0.00E+00 | 0.00E+00 | 0.00E+00 | 2.25E−06 | 5.27E−05 | 1.08E−05 | 3.77E−04 |
| $H_2S$ | 1.32E−05 | 0.00E+00 | 1.00E+00 | 2.19E−05 | 5.73E−07 | 5.51E−07 | 7.42E−07 |
| Methyl Mercaptan | 0.00E+00 | 0.00E+00 | 0.00E+00 | 3.00E−08 | 1.08E−06 | 7.58E−07 | 3.54E−06 |
| Dimethyl Sulfide | 0.00E+00 | 0.00E+00 | 0.00E+00 | 1.63E−06 | 5.30E−05 | 2.37E−04 | 2.81E−04 |

TABLE 2B

| Component (mole fraction) | Line No | | | | | | |
|---|---|---|---|---|---|---|---|
| | 51 | 53 | 63 | 64-68 | 69 | 71 | 72 |
| $N_2$ | 7.37E−03 | 7.90E−04 | 4.65E−03 | 5.85E−10 | 5.85E−35 | 1.80E−06 | 2.08E−02 |
| $O_2$ | 1.00E−14 | 1.23E−15 | 0.00E+00 | 0.00E+00 | 0.00E+00 | 0.00E+00 | 2.03E−14 |
| Ar | 6.35E−03 | 7.80E−04 | 5.05E−03 | 2.69E−09 | 2.11E−35 | 3.38E−06 | 1.24E−02 |
| $H_2O$ | 1.60E−02 | 5.75E−02 | 4.92E−04 | 1.50E−03 | 1.12E−01 | 2.57E−02 | 7.67E−06 |
| $H_2$ | 1.14E−01 | 1.07E−02 | 5.63E−02 | 1.36E−09 | 2.88E−35 | 1.22E−05 | 4.08E−01 |
| CO | 1.29E−01 | 1.48E−02 | 9.20E−02 | 2.52E−08 | 6.47E−35 | 5.15E−05 | 3.26E−01 |
| $CO_2$ | 3.08E−01 | 7.24E−02 | 6.32E−01 | 2.03E−04 | 1.23E−35 | 1.95E−02 | 2.58E−02 |
| $CH_4$ | 1.65E−01 | 2.36E−02 | 1.66E−01 | 4.82E−07 | 7.23E−35 | 3.58E−04 | 2.04E−01 |
| $C_2H_6$ | 2.78E−03 | 6.49E−04 | 5.60E−06 | 2.05E−06 | 2.05E−35 | 1.29E−04 | 1.03E−03 |
| $C_3H_8$ | 4.37E−04 | 1.58E−04 | 1.47E−03 | 8.18E−06 | 5.80E−35 | 5.23E−05 | 7.05E−05 |
| 1,5-Hexadiene | 0.00E+00 | 0.00E+00 | 0.00E+00 | 0.00E+00 | 0.00E+00 | 0.00E+00 | 0.00E+00 |
| N-Butane | 4.60E−05 | 1.97E−05 | 1.85E−04 | 3.23E−06 | 1.02E−35 | 1.23E−05 | 3.76E−07 |
| N-Pentane | 4.77E−04 | 3.37E−04 | 2.25E−04 | 3.31E−04 | 1.60E−35 | 4.00E−04 | 1.53E−05 |
| N-Hexane | 1.52E−05 | 2.25E−05 | 4.46E−05 | 4.55E−05 | 2.46E−27 | 2.63E−05 | 3.77E−06 |
| Formaldehyde | 3.91E−06 | 5.89E−05 | 3.11E−10 | 1.71E−20 | 1.11E−04 | 1.47E−06 | 1.16E−11 |
| Acetaldehyde | 1.04E−03 | 2.55E−03 | 5.86E−04 | 6.53E−03 | 7.92E−14 | 4.26E−03 | 1.19E−05 |
| N-Propionaldehyde | 2.78E−04 | 8.28E−04 | 5.21E−05 | 2.37E−03 | 1.92E−09 | 2.11E−03 | 4.51E−06 |
| Dimethyl Ether | 1.26E−04 | 9.66E−05 | 6.47E−05 | 7.93E−05 | 6.03E−35 | 5.83E−05 | 1.27E−06 |
| MeOH | 1.12E−01 | 3.19E−01 | 1.51E−02 | 8.52E−01 | 7.05E−03 | 6.39E−01 | 6.96E−04 |
| EtOH | 1.09E−01 | 3.88E−01 | 4.17E−03 | 4.10E−02 | 7.42E−01 | 2.14E−01 | 1.14E−04 |
| PrOH | 1.13E−02 | 5.93E−02 | 6.51E−05 | 1.20E−06 | 1.15E−01 | 1.61E−02 | 2.97E−06 |
| Isopropanol | 3.54E−04 | 1.38E−03 | 7.28E−06 | 1.32E−05 | 2.71E−03 | 5.59E−04 | 1.25E−07 |
| N-Butanol | 8.49E−04 | 6.45E−03 | 6.07E−07 | 9.93E−12 | 1.23E−02 | 7.89E−04 | 3.02E−08 |
| Isobutanol | 2.89E−04 | 1.88E−03 | 5.73E−07 | 5.36E−10 | 3.61E−03 | 3.57E−04 | 2.68E−08 |
| 1-Pentanol | 1.08E−04 | 1.20E−03 | 1.28E−08 | 7.95E−16 | 2.28E−03 | 8.96E−05 | 1.39E−09 |
| Formic Acid | 1.84E−06 | 1.12E−05 | 1.22E−08 | 7.63E−10 | 2.21E−05 | 4.42E−06 | 2.03E−09 |

TABLE 2B-continued

| Component | Line No | | | | | | |
|---|---|---|---|---|---|---|---|
| (mole fraction) | 51 | 53 | 63 | 64-68 | 69 | 71 | 72 |
| Propionic Acid | 4.35E−14 | 8.68E−13 | 8.28E−19 | 1.27E−28 | 1.63E−12 | 0.00E+00 | 0.00E+00 |
| Acetone | 2.39E−04 | 6.00E−04 | 1.22E−04 | 1.55E−03 | 2.37E−13 | 1.05E−03 | 3.67E−06 |
| Methyl Ethyl Ketone | 6.50E−05 | 2.21E−04 | 7.78E−06 | 6.36E−04 | 4.58E−07 | 5.71E−04 | 1.12E−06 |
| Methyl Formate | 5.08E−04 | 5.70E−04 | 2.11E−03 | 9.53E−04 | 9.66E−33 | 7.18E−04 | 5.42E−06 |
| Methyl Acetate | 4.42E−03 | 1.00E−02 | 3.82E−03 | 2.44E−02 | 7.62E−15 | 1.40E−02 | 6.61E−05 |
| Ethyl Acetate | 5.24E−03 | 1.55E−02 | 1.3W−3 | 4.33E−02 | 2.70E−08 | 3.61E−02 | 1.01E−04 |
| Methyl Propionate | 1.53E−03 | 4.67E−03 | 3.20E−04 | 1.34E−02 | 7.26E−09 | 1.22E−02 | 5.14E−05 |
| Ethyl Propionate | 8.36E−04 | 2.88E−03 | 1.27E−04 | 8.51E−03 | 6.71E−08 | 8.16E−03 | 5.39E−05 |
| Propyl Acetate | 3.50E−04 | 1.72E−03 | 1.19E−05 | 9.39E−04 | 2.96E−03 | 2.22E−03 | 6.87E−06 |
| Methyl Butyrate | 9.13E−05 | 3.77E−04 | 6.60E−06 | 1.06E−03 | 3.08E−05 | 9.82E−04 | 4.56E−06 |
| $H_2S$ | 1.59E−06 | 7.42E−07 | 6.89E−06 | 1.10E−07 | 1.02E−35 | 3.12E−07 | 1.47E−08 |
| Methyl Mercaptan | 3.57E−06 | 3.54E−06 | 1.71E−05 | 4.56E−06 | 8.92E−35 | 2.73E−06 | 5.89E−06 |
| Dimethyl Sulfide | 1.47E−04 | 2.81E−04 | 2.98E−04 | 6.08E−04 | 2.89E−20 | 2.67E−04 | 3.31E−06 |

TABLE 2C

| Component | Line No | | | |
|---|---|---|---|---|
| (mole fraction) | 73 | 74 | 91 | 92 |
| $N_2$ | 7.46E−03 | 8.98E−04 | 0.00E+00 | 2.29E−10 |
| $O_2$ | 1.13E−14 | 0.00E+00 | 0.00E+00 | 0.00E+00 |
| Ar | 6.86E−03 | 1.13E−03 | 0.00E+00 | 1.05E−09 |
| $H_2O$ | 3.26E−05 | 5.45E−05 | 1.14E−01 | 5.88E−04 |
| $H_2$ | 1.05E−01 | 9.64E−03 | 0.00E+00 | 5.32E−10 |
| CO | 1.54E−01 | 2.13E−02 | 0.00E+00 | 9.86E−09 |
| $CO_2$ | 4.82E−01 | 8.54E−01 | 0.00E+00 | 7.95E−05 |
| $CH_4$ | 2.33E−01 | 6.98E−02 | 0.00E+00 | 1.89E−07 |
| $C_2H_6$ | 4.97E−03 | 6.23E−03 | 0.00E+00 | 6.89E−07 |
| $C_3H_8$ | 6.25E−04 | 1.55E−03 | 0.00E+00 | 3.20E−06 |
| 1,5-Hexadiene | 0.00E+00 | 0.00E+00 | 0.00E+00 | 0.00E+00 |
| N-Butane | 1.45E−07 | 1.64E−04 | 0.00E+00 | 1.27E−06 |
| N-Pentane | 1.18E−04 | 1.88E−03 | 0.00E+00 | 1.29E−04 |
| N-Hexane | 7.38E−06 | 0.00E+00 | 0.00E+00 | 1.78E−05 |
| Formaldehyde | 1.15E−10 | 8.93E−12 | 5.92E−06 | 6.02E−03 |
| Acetaldehyde | 5.14E−05 | 6.44E−04 | 8.01E−14 | 2.56E−03 |
| N-Propionaldehyde | 1.58E−05 | 3.93E−05 | 1.94E−09 | 9.27E−04 |
| Dimethyl Ether | 1.38E−05 | 2.74E−04 | 0.00E+00 | 3.10E−05 |
| MeOH | 2.24E−03 | 1.94E−02 | 7.13E−03 | 3.34E−01 |
| EtOH | 3.40E−04 | 6.62E−04 | 7.50E−01 | 1.64E−02 |
| PrOH | 8.38E−06 | 2.86E−06 | 1.16E−01 | 3.29E−02 |
| Isopropanol | 4.99E−07 | 5.98E−07 | 2.74E−03 | 1.29E−05 |
| N-Butanol | 1.01E−07 | 1.19E−08 | 4.87E−03 | 4.28E−01 |
| Isobutanol | 9.12E−08 | 1.63E−08 | 3.17E−03 | 2.72E−02 |
| 1-Pentanol | 4.09E−07 | 1.25E−10 | 2.85E−04 | 1.14E−01 |
| Formic Acid | 6.64E−09 | 5.99E−10 | 2.22E−05 | 4.81E−06 |
| Propionic Acid | 0.00E+00 | 0.00E+00 | 7.56E−14 | 8.91E−11 |
| Acetone | 1.20E−05 | 1.67E−04 | 2.39E−13 | 6.07E−04 |
| Methyl Ethyl Ketone | 3.34E−06 | 7.97E−06 | 4.63E−07 | 2.49E−04 |
| Methyl Formate | 2.61E−05 | 8.63E−06 | 0.00E+00 | 3.73E−04 |
| Methyl Acetate | 2.38E−04 | 4.12E−03 | 7.70E−15 | 9.57E−03 |
| Ethyl Acetate | 2.84E−04 | 2.33E−03 | 2.73E−08 | 1.70E−02 |
| Methyl Propionate | 1.29E−04 | 3.16E−03 | 7.34E−09 | 5.26E−03 |
| Ethyl Propionate | 9.42E−05 | 1.15E−04 | 6.79E−08 | 3.33E−03 |
| Propyl Acetate | 1.32E−05 | 1.72E−05 | 2.99E−03 | 3.76E−04 |
| Methyl Butyrate | 8.10E−06 | 3.48E−06 | 3.11E−05 | 4.14E−04 |
| $H_2S$ | 7.66E−07 | 4.40E−06 | 0.00E+00 | 4.32E−08 |
| Methyl Mercaptan | 3.84E−07 | 7.33E−06 | 0.00E+00 | 1.79E−06 |
| Dimethyl Sulfide | 1.15E−05 | 2.12E−04 | 0.00E+00 | 2.38E−04 |

TABLE 3

| Line Number | Flow Rate (kg/hr) | Temp (° C.) | Pressure (bar/MPa) |
|---|---|---|---|
| 11 | 260000 | 40 | 70/7 |
| 13 | 346531 | 120 | 70/7 |
| 23 | 0 | 30 | 230/23 |
| 25 | 1716051 | 128 | 215/21.5 |
| 31 | 1836051 | 50 | 124/12.4 |
| 41 | 1456577 | 50 | 124/12.4 |
| 42 | 379481 | 50 | 124/12.4 |
| 43 | 1376576 | 50 | 124/12.4 |
| 44 | 80000 | 50 | 124/12.4 |
| 51 | 13693 | 158 | 75/7.5 |
| 53 | 379472 | 50 | 124/12.4 |
| 63 | 250 | 40 | 16/1.6 |
| 64 | 162722 | 72 | 2/0.2 |
| 65 | 132722 | 73 | 25/2.5 |
| 66 | 30000 | 40 | 25/2.5 |
| 67 | 11450 | 76 | 75/7.5 |
| 68 | 120000 | 73 | 25/2.5 |
| 69 | 221977 | 96 | 6/0.6 |
| 71 | 50350 | 151 | 25/2.5 |
| 72 | 808074 | 45 | 120/12 |
| 73 | 239105 | 1 | 16/1.6 |
| 74 | 340266 | 123 | 70/7 |
| 91 | 218026 | 40 | 5/0.5 |
| 92 | 5223 | 40 | 6/0.6 |

COMP EX A

The ASPEN simulation data presented in Tables 2A through 2C and 3 above contemplate splitting a stream having the composition for line 41 into two portions, one directed to synthesis gas generator 20 via line 44 and one directed to $CO_2$ absorption and separation unit 70 via line 43.

If one sends all of the composition in line 41 to $CO_2$ absorption and separation unit 70 and eliminates sending any portion to synthesis gas generator 20, it is believed that the second lights recycle stream that exits $CO_2$ absorption and separation unit 70 via line 72 will contain an increased content of light hydrocarbons (e.g. $CH_4$ and $C_2H_6$) relative to that shown in Table 2B. It is also believed that this leads, in turn, to a build up of such light hydrocarbons in feedstreams and recycle streams that enter MAS reactor 30, thereby displacing synthesis gas components (CO and $H_2$) and effectively reducing output of desired mixed alcohols.

One means of countering build-up of light hydrocarbons in streams that enter MAS reactor 30 is to purge, vent or otherwise directing a portion of contents in line 44 outside the process schematically depicted in FIG. 1 before they reach synthesis gas generator 20. It is believed that purging 6.2% of the contents of line 41 rather than sending all of the contents of line 44 to synthesis gas generator 20 reduces carbon utilization from 55% to 49%. A reduced carbon utilization translates to an increase in cost of producing mixed alcohols based upon loss of carbon values contained in a given aliquot of synthesis gas.

EX 2

As a reactor chamber, use a ten inch (25.4 cm) length of stainless steel tubing that has an O.D. of one inch (2.5 cm) and a wall thickness of 0.035″ (0.89 mm) and is equipped with an inlet pressure transducer at one end and an outlet pressure transducer at the other end. Fill the tube with 20 grams (g) of the same catalyst as in Ex 1 and sufficient inert quartz chips to occupy volume not taken up by the catalyst. Use $H_2$ to pressurize the inside of the tube to a pressure of 478 pounds per square inch gauge (psig) (3.27 MPa). Into the tubing end equipped with the inlet pressure transducer, feed $H_2$ at a rate of 386 sccm through a first Brooks 5850E mass flow controller and CO at a rate of approximately 425 sccm through a second Brooks 5850E mass flow controller. In addition, feed methyl acetate (MeAc) to the same end at a rate of 0.2 ml per minute using a Gilson 307 pump equipped with a 5SC head. Heat the reactor chamber and its contents with six spaced apart one inch (2.5 cm) inner diameter band heaters (Watlow).

GC analysis of reaction products from the reactor chamber shows that MeOH, EtOH, MeAc and ethyl acetate (EtAc) are present.

Calculate percent (%) MeAc conversion by multiplying 100 times the quotient of a numerator that is a sum of two times the number of moles of product EtAc plus moles of product EtOH and a denominator that is a sum of moles of product MeAc plus two times moles of product EtAc plus moles of product EtOH. As used herein, e.g. in modifying EtAc, "product: refers to EtAc contained in a raw product stream from a reactor such as MAS reactor 30.

Table 4 below shows product content in terms of wt % MeOH, wt % EtOH, wt % MeAc and wt % EtAc together with reaction temperature (Temp ° C.) and conversion.

TABLE 4

| Temp ° C./Product content and Conversion | MeOH (wt %) | EtOH (wt %) | MeAc (wt %) | EtAc (wt %) | Conversion (%) |
|---|---|---|---|---|---|
| 220 | 2.2 | 7.8 | 88.3 | 1.7 | 14.8 |
| 240 | 5.7 | 20.0 | 71.7 | 2.6 | 33.8 |
| 260 | 14.4 | 44.3 | 40.8 | 0.5 | 63.9 |
| 280 | 22.3 | 54.9 | 22.8 | 0 | 79.5 |
| 300 | 27.4 | 61.8 | 10.8 | 0 | 90.2 |
| 320 | 24.4 | 72.8 | 2.8 | 0 | 97.7 |

EX 3

Replicate Ex 2, but reduce the pressure to 450 psig (3.1 MPa), feed EtAc rather than MeAc and change the feed rate of EtAc from 0.2 ml/minute to a liquid hourly space velocity (LHSV) of 0.6, which is sufficient to provide a molar ratio of $H_2$ to EtAc of 5.68.

EtAc conversion (%)=100×(0.5 times moles of EtOH)/(moles EtAc in the feed plus 0.5 times moles of EtOH), where moles of EtOH represents moles of EtOH in product from the reactor.

EtAc conversion numbers and associated temperatures are: 200° C.=0%; 240° C.=7%; 260° C.=35%; 280° C.=65%; 300° C.=81%; and 320° C.=92%.

Ex 3 shows that EtAc is less reactive than MeAc. Nonetheless, both MeAc and EtAc yield relatively high conversions to desired products at conversion temperatures of at least 300° C.

EX 4

Replicate Ex 3, but substitute propyl acetate (PrAc) for EtAc to provide a molar ratio of $H_2$ to PrAc of 10.3, increase the pressure to 500 psig (3.4 MPa), eliminate runs at 200° C. and 240° C., and change the formula to calculate conversion to 100 times moles of propanol (PrOH) in the product divided by the sum of moles of PrAc (feed) plus moles of PrOH (product).

PrAc conversion numbers and associated temperatures are: 260° C.=32.8%; 280° C.=61.5%; 300° C.=82.3%; and 320° C.=91.9%.

The data in Ex 2 through Ex 4 show that even at relatively low pressures such as 500 psig (3.4 MPa) or less, lower alkyl acetate (MeAc, EtAc and PrAc) conversion to corresponding alcohols exceeds 80% at temperatures as low as 300° C. Tables 2A through 2C show ASPEN simulation projections of lower alkyl acetate contents in various lines. Such data and projections also show that recycle of lower alkyl acetates appears to improve process economics by increasing carbon utilization over that inherent in prior practices that promote elimination of such lower alkyl acetates. As it is believed that separation of lower alkyl acetates from MeOH presents considerable technical challenges and incurs considerable cost, an ability to recycle such lower alkyl acetates together with MeOH and simultaneously increase carbon utilization appears to be economically attractive.

COMP EX B

The ASPEN simulation data presented in Tables 2A through 2C and 3 above contemplate using a portion of an ethanol light fraction to facilitate removal of at least a portion of $CO_2$ and inert gases from the process illustrated in FIG. 1. Such removal occurs in $CO_2$ absorption and separation unit 70.

If one returns all of the ethanol light fraction to synthesis gas generator 20 by eliminating line 66 yet chooses to maintain at least some level of $CO_2$ elimination, certain alternate technologies are available, but at a cost. Skilled artisans recognize that the RECTISOLT™ process disclosed above requires use of pure MeOH. This entails added capital costs consistent with apparatus and processes used to purify MeOH. Skilled artisans also recognize that one may also use a solvent known as SELEXOL™ (a dimethyl ether of polyethylene glycol) provided one also accepts effectively precluded from returning a heavy products recycle stream to third separation unit 60 via line 71 because of contamination by the solvent. By losing an ability to return the heavy products recycle stream in this or a similar fashion, one effectively lowers recovery of desired mixed alcohols.

COMP EX C

As a further variation of Comp Ex B, one can eliminate use of $CO_2$ absorption and separation unit 70 entirely in favor of dividing contents of the stream in line 41 into three fractions. The three fractions are (a) a first fraction that is recycled to synthesis gas generator 20, (b) a second fraction that is recycled to MAS reactor 30, and (c) a third fraction that is vented, purged from the process illustrated in FIG. 1 or sent to another process outside that illustrated in FIG. 1 for further processing. The second fraction is limited by an upper limit imposed upon CO2 concentration in a reaction to convert synthesis gas to a raw product stream in MAS reactor 30. The first fraction is limited by selection of a desired synthesis gas composition ($H_2$ to CO ratio). With these limitations on the first and second fractions, the third fraction may well constitute a sizeable fraction. ASPEN simulation of such an arrangement yields a carbon utilization of 44% as opposed to 55% by using the full process illustrated in FIG. 1 and exemplified in Ex 1.

What is claimed is:

1. A process for selectively producing mixed alcohols, the process comprising steps as follows:
    A. generating a synthesis gas feedstock, said feedstock comprising carbon monoxide and hydrogen;
    B. contacting the synthesis gas feedstock with a mixed alcohol synthesis catalyst under conditions sufficient to produce a crude product stream;
    C. effecting separation of the crude product stream into at least a first lights product stream and a heavy products stream;
    D. optionally recycling a portion of the first lights product stream to step A or to a precursor to step A where said recycle stream combines with, respectively, synthesis gas or a precursor to synthesis gas;
    E. separating the heavy products stream into at least two fractions, an ethanol-light fraction and an ethanol-heavy fraction;
    F. forming a combined stream by placing at least a portion of the first lights product stream in operative contact with at least a portion of the ethanol-light fraction whereby the ethanol-light fraction functions as an absorption medium to effect absorption of at least a portion of carbon dioxide and inert gas contained in said first lights product stream;
    G. optionally recycling at least a portion of the ethanol-light fraction to at least one of step A, step B or a precursor to step A, where said recycle stream combines with synthesis gas if it goes to step A or step B, or a precursor to synthesis gas if it goes to a precursor to step A;
    H. separating the combined stream into a second lights product stream, a heavy products recycle stream, a carbon dioxide-rich recycle stream, and a purge gas fraction, the purge gas fraction comprising at least a portion of carbon dioxide and inert gases contained in the combined stream;
    I. optionally recycling the second lights product stream to step B. where said second lights product stream combines with the synthesis gas feedstock; and
    J. recycling the heavy products recycle stream to step E;
    K. optionally recycling the carbon dioxide-rich recycle stream to step A or a precursor to step A where said recycle stream combines with, respectively, synthesis gas or a precursor to synthesis gas; and
    L. removing the purge gas fraction from the process for at least one of venting to the atmosphere, use as fuel gas or use in a separate process.

2. A process for selectively producing mixed alcohols, the process comprising steps as follows:
    A. generating a synthesis gas feedstock, said feedstock comprising carbon monoxide and hydrogen;
    B. contacting the synthesis gas feedstock with a mixed alcohol synthesis catalyst under conditions sufficient to produce a crude product stream;
    C. effecting separation of the crude product stream into at least a first lights product stream and a heavy products stream;
    D. splitting the first lights product stream into a first lights product portion and a second lights product portion;
    E. recycling the first lights product portion to step A or to a precursor to step A where said first lights product portion combines with, respectively, synthesis gas or a precursor to synthesis gas;
    F. effecting separation of the heavy products stream into a spent gas stream and a purified heavy products stream;
    G. recycling the spent gas stream to step A or to a precursor to step A where said spent gas stream combines with, respectively, synthesis gas or a precursor to synthesis gas;
    H. separating the purified heavy products stream into at least two fractions, an ethanol-light fraction and an ethanol-heavy fraction;
    I. recycling at least a portion of the ethanol-light fraction to at least one of step A, step B or a precursor to step A, where said recycle stream combines with synthesis gas if it goes to step A or step B, or a precursor to synthesis gas if it goes to a precursor to step A;
    J. forming a combined stream by placing the first lights product portion in operative contact with at least a portion of the ethanol-light fraction whereby the ethanol-light fraction functions as an absorption medium to effect absorption of at least a portion of carbon dioxide and inert gas contained in said first lights product portion;
    K. separating the combined stream into a second lights product stream, a heavy products recycle stream, a carbon dioxide-rich recycle stream, and a purge gas fraction, the purge gas fraction comprising at least a portion of carbon dioxide and inert gases contained in the combined stream;
    L. recycling the second lights product stream to step B. where said second lights product stream combines with the synthesis gas feedstock; and
    M. recycling the heavy products recycle stream to step H;
    N. recycling the carbon dioxide-rich recycle stream to step A or a precursor to step A where said recycle stream combines with, respectively, synthesis gas or a precursor to synthesis gas; and
    O. removing the purge gas fraction from the process for at least one of venting to the atmosphere, use as fuel gas or use in a separate process.

3. The process of claim 1 or claim 2, wherein the first lights product stream comprises unreacted carbon monoxide, unreacted hydrogen, carbon dioxide, methane, ethane and inert gases (Ar and $N_2$).

4. The process of claim 1 or claim 2, wherein the heavy products stream comprises methanol, ethanol, propanol, butanol, pentanol, esters, aldehydes, water, dissolved synthesis gas, and light hydrocarbons ($CH_4$, $C_2H_6$, and $C_3H_8$).

5. The process of claim 1 or claim 2, wherein synthesis gas feedstock generation in step A occurs via at least one of partial oxidation of natural gas, steam reforming of natural gas or autothermal reforming of natural gas.

6. The process of claim 1 or claim 2, wherein the synthesis gas feedstock is combined with a sulfur source prior to contact with the mixed alcohol synthesis catalyst in step B.

7. The process of claim 1 or claim 2, wherein synthesis gas generation occurs by way of gasifying coal or another carbonaceous material.

8. The process of claim 1 or claim 2, wherein the mixed alcohol synthesis catalyst is a cobalt/molybdenum sulfide catalyst.

9. The process of claim 1, further comprising a step M, which follows step E and comprises subjecting the ethanol-heavy stream to dehydration conditions, including exposure to a dehydration catalyst, sufficient to convert at least ethanol to ethylene and, optionally, propanol to propylene and, optionally, butanol to butylene.

10. The process of claim 2, further comprising a step P, which follows step H and comprises subjecting the ethanol-heavy stream to dehydration conditions, including exposure to a dehydration catalyst, sufficient to convert at least ethanol to ethylene and, optionally, propanol to propylene and, optionally, butanol to butylene.

11. The process of claim 9, further comprising a sequential step N that follows step M, step N comprising subjecting at least one olefin to polymerization conditions sufficient to form a homopolymer of a single olefin monomer, a copolymer of a single olefin monomer and a second monomer that is copolymerizable with the single olefin monomer or an interpolymer of a single olefin monomer and at least two other monomers that are copolymerizable with the single olefin monomer.

12. The process of claim 10, further comprising a sequential step Q that follows step P, step Q comprising subjecting at least one olefin to polymerization conditions sufficient to form a homopolymer of a single olefin monomer, a copolymer of a single olefin monomer and a second monomer that is copolymerizable with the single olefin monomer or an interpolymer of a single olefin monomer and at least two other monomers that are copolymerizable with the single olefin monomer.

13. The process of claim 10 or claim 12, wherein the dehydration catalyst is alumina.

14. The process of claim 9, wherein the ethanol-heavy fraction is further subdivided, in a step E', into a first product alcohol fraction comprising ethanol and propanol and a second product alcohol fraction comprising butanol, step E' occurring subsequent to step E, but prior to step M.

15. The process of claim 14, wherein step M is modified to a step M' wherein each of the first product alcohol fraction and the second product alcohol fraction are separately subjected to dehydration conditions, such dehydration conditions being sufficient to convert at least one of ethanol and propanol in the first product alcohol fraction to, respectively, ethylene and propylene, and at least butanol in the second product alcohol fraction to butylene.

16. The process of claim 10, wherein the ethanol-heavy fraction is further subdivided, in a step H', into a first product alcohol fraction comprising ethanol and propanol and a second product alcohol fraction comprising butanol, step H' occurring subsequent to step H, but prior to step P.

17. The process of claim 16, wherein step P is modified to a step P' wherein each of the first product alcohol fraction and the second product alcohol fraction are separately subjected to dehydration conditions, such dehydration conditions being sufficient to convert at least one of ethanol and propanol in the first product alcohol fraction to, respectively, ethylene and propylene, and at least butanol in the second product alcohol fraction to butylenes.

18. The process of claim 1, wherein a third fraction is separated from the heavy products stream in step E, the third fraction being a LP gas fraction.

19. The process of claim 2, wherein a third fraction is separated from the purified heavy products stream in step H, the third fraction being a LP gas fraction.

20. The process of claim 1, further comprising a step A', step A' being intermediate between steps A and B and comprising removing an amount of water from the synthesis gas to yield a reduced water content synthesis gas stream for step B.

21. The process of claim 2, further comprising a step A', step A' preceding at least one of steps A and B and comprising removing an amount of water from at least one of synthesis gas from step A, the ethanol-light fraction from step I, the first light products portion from step E or the spent gas stream from step G, such water removal effectively providing a reduced water content synthesis gas stream for step B.

* * * * *